United States Patent [19]
Pall et al.

[11] Patent Number: 5,501,795
[45] Date of Patent: * Mar. 26, 1996

[54] DEVICE FOR DEPLETION OF THE LEUCOCYTE CONTENT OF BLOOD AND BLOOD COMPONENTS

[75] Inventors: David B. Pall, Roslyn Estates; Thomas C. Gsell, Glen Cove, both of N.Y.

[73] Assignee: Pall Corporation, East Hills, N.Y.

[*] Notice: The portion of the term of this patent subsequent to Sep. 6, 2011, has been disclaimed.

[21] Appl. No.: 277,426

[22] Filed: Jul. 18, 1994

Related U.S. Application Data

[63] Continuation of Ser. No. 71,990, Jun. 7, 1993, Pat. No. 5,344,561, which is a continuation of Ser. No. 719,506, Jun. 24, 1991, Pat. No. 5,229,012, which is a continuation-in-part of Ser. No. 527,717, May 22, 1990, abandoned, which is a continuation-in-part of Ser. No. 349,439, May 9, 1989, abandoned.

[51] Int. Cl.$^6$ .................... B01D 27/02; B01D 39/02
[52] U.S. Cl. .................... 210/508; 210/295; 210/435; 210/446; 210/489; 210/490; 210/491; 210/505
[58] Field of Search .................... 210/435, 446, 210/489, 490, 491, 505, 508, 496, 321.84, 295, 321.85; 422/101, 102

[56] References Cited

U.S. PATENT DOCUMENTS

| | | | |
|---|---|---|---|
| 2,834,730 | 5/1958 | Painter et al. | 210/504 |
| 3,448,041 | 6/1969 | Swank . | |
| 3,593,854 | 7/1971 | Swank | 210/446 |
| 3,765,536 | 10/1973 | Rosenberg | 210/446 |
| 3,905,905 | 9/1975 | O'Leary et al. | 210/436 |
| 3,935,110 | 1/1976 | Schmid et al. | 210/445 |
| 3,935,111 | 1/1976 | Bentley | 210/446 |
| 3,954,621 | 5/1976 | Etani et al. | 210/314 |
| 4,009,714 | 3/1977 | Hammer | 210/445 |
| 4,009,715 | 3/1977 | Forberg et al. | 210/455 |
| 4,056,476 | 11/1977 | Mouwen et al. | 210/446 |
| 4,073,732 | 2/1978 | Lauer et al. | 210/491 |
| 4,087,363 | 5/1978 | Rosemeyer et al. | 210/489 |
| 4,092,246 | 5/1978 | Kummer | 210/504 |
| 4,111,199 | 9/1978 | Djerassi . | |
| 4,116,845 | 9/1978 | Swank | 210/440 |
| 4,157,967 | 6/1979 | Meyst et al. | 210/449 |

(List continued on next page.)

FOREIGN PATENT DOCUMENTS

| | | |
|---|---|---|
| 0045476 | 2/1982 | European Pat. Off. . |
| 0155003 | 9/1985 | European Pat. Off. . |
| 0267286 | 5/1988 | European Pat. Off. . |
| 0312595 | 4/1989 | European Pat. Off. . |
| 0315022 | 5/1989 | European Pat. Off. . |
| 0370584 | 5/1990 | European Pat. Off. . |
| 2222951 | 7/1974 | Germany . |
| 1575753 | 9/1980 | United Kingdom . |
| 2056301 | 3/1981 | United Kingdom . |

OTHER PUBLICATIONS

Vox Sanguinis, vol. 23, 1972, pp. 308–320, Diepenhosrt et al., "Removal of Leukocytes From Whole Blood . . . Cotton Wool".

Pall Biomedical Products Corporation, S–PL100 Brochure, Rev. E, pp. 3–7, "Pall PL 100® Leukocyte Removal . . . Transfusion" (undated).

Pall Biomedical Products Corporation, RC50RC100 Brochure, pp. 2–7, "Pall RC50™ and RC100™ Leukocyte Removal . . . Bedside" (undated).

Primary Examiner—John Kim
Attorney, Agent, or Firm—Leydig, Voit & Mayer

[57] ABSTRACT

A high efficiency leucocyte-depletion filter for use with packed red cell concentrate derived from freshly drawn blood comprises a fibrous filter medium with a pore size of from about 0.5 to less than 3.6 µm and a CWST of from 53 to about 80. The filter is preferably used in conjunction with a gel prefilter and, optionally, a microaggregate filter so as to minimize clogging. In a preferred embodiment, the voids volume is about 60% to about 85%.

31 Claims, 2 Drawing Sheets

U.S. PATENT DOCUMENTS

| | | | |
|---|---|---|---|
| 4,229,306 | 10/1980 | Hein et al. | 210/446 |
| 4,246,107 | 5/1981 | Takenaka et al. | 210/767 |
| 4,283,289 | 8/1981 | Meyst et al. | 210/448 |
| 4,294,594 | 10/1981 | Sloane, Jr. et al. | 210/446 |
| 4,330,410 | 5/1982 | Takenaka et al. | 210/767 |
| 4,370,381 | 1/1983 | Horikoshi et al. | 210/508 |
| 4,376,675 | 3/1983 | Perrotta | 210/509 |
| 4,416,777 | 11/1983 | Kuroda et al. | 210/446 |
| 4,422,939 | 12/1983 | Sharp et al. | 210/445 |
| 4,476,023 | 10/1984 | Horikoshi et al. | 210/446 |
| 4,477,575 | 10/1984 | Vogel et al. | 210/509 |
| 4,534,757 | 8/1985 | Geller | 604/85 |
| 4,604,208 | 8/1986 | Chu et al. | 210/636 |
| 4,608,173 | 10/1986 | Watanabe et al. | 210/491 |
| 4,617,124 | 10/1986 | Pall et al. | 210/508 |
| 4,618,533 | 10/1986 | Steuck | 427/245 |
| 4,636,312 | 1/1987 | Willis | 210/416.1 |
| 4,675,117 | 6/1987 | Neumann et al. | 210/789 |
| 4,701,267 | 10/1987 | Watanabe et al. | 210/806 |
| 4,810,378 | 3/1989 | Carmen et al. | 210/206 |
| 4,861,617 | 8/1989 | Pall et al. | 427/2 |
| 4,880,548 | 11/1989 | Pall et al. | 210/508 |
| 4,915,848 | 4/1990 | Carmen et al. | 210/749 |
| 4,923,620 | 5/1990 | Pall | 210/767 |
| 4,925,572 | 5/1990 | Pall | 210/767 |
| 4,936,998 | 6/1990 | Nishimura et al. | 210/767 |
| 4,943,287 | 7/1990 | Carmen | 604/408 |
| 4,959,150 | 9/1990 | Degen | 210/638 |
| 4,963,260 | 10/1990 | Naoi et al. | 210/446 |
| 4,985,153 | 1/1991 | Kuroda et al. | 210/782 |
| 4,997,577 | 3/1991 | Stewart | 210/767 |
| 5,028,332 | 7/1991 | Ohnishi | 210/500.34 |
| 5,100,564 | 3/1992 | Pall et al. | 210/782 |
| 5,152,905 | 10/1992 | Pall et al. | 210/767 |
| 5,164,087 | 11/1992 | Naoi et al. | 210/500.1 |
| 5,217,627 | 6/1993 | Pall et al. | 210/767 |
| 5,229,012 | 7/1993 | Pall et al. | 210/508 |
| 5,258,127 | 11/1993 | Gsell et al. | 210/767 |
| 5,316,674 | 6/1994 | Pall et al. | 210/257 |
| 5,344,561 | 9/1994 | Pall et al. | 210/508 |

DEVICE FOR DEPLETION OF THE LEUCOCYTE CONTENT OF BLOOD AND BLOOD COMPONENTS

This application is a continuation of application Ser. No. 08/071,990, filed Jun. 7, 1993, now U.S. Pat. No. 5,344,561, which is a continuation of Ser. No. 07/719,506, filed Jun. 24, 1991, now U.S. Pat. No. 5,229,012, which is a continuation-in-part of U.S. patent application Ser. No. 07/527,717, filed May 22, 1990, now abandoned, which, in turn, is a continuation-in-part of U.S. patent application Ser. No. 07/349,439, filed May 9, 1989 (now abandoned).

TECHNICAL FIELD

This invention relates to a method for depleting the leucocyte content of whole blood and products derived therefrom, particularly from human packed red blood cells, and more particularly from anti-coagulated human packed red blood (PRC) cells which have been derived from whole blood freshly drawn from a blood donor.

BACKGROUND OF THE INVENTION

It has been the practice for 50 years or more to transfuse whole blood, and more recently blood components, from one or more donors to other persons. With the passage of time and accumulation of research and clinical data, transfusion practices have improved greatly. One aspect of current practice is that whole blood is rarely administered; rather, patients needing red blood cells are given packed red cells (hereinafter PRC), and patients needing platelets are given platelet concentrate. These components are separated from whole blood by centrifuging, the process providing, as a third product, plasma, from which various other useful components are obtained. In addition to the three above-listed components, whole blood contains white blood cells (known collectively as leucocytes) of various types, of which the most important are granulocytes and lymphocytes. White blood cells provide protection against bacterial and viral infection.

In the mid to late seventies, a number of investigators proposed that granulocytes be separated from donated blood and transfused into patients who lacked them, for example, those whose own cells had been overwhelmed by an infection. In the resulting investigations, it became apparent that this practice is generally harmful, since patients receiving such transfusion developed high fevers, had other adverse reactions, and often rejected the transfused cells. Further, the transfusion of packed cells or whole blood containing donor leucocytes can be harmful to the recipient in other ways. Some of the viral diseases induced by transfusion therapy, e.g., Cytomegaloviral Inclusion Disease, which is a life threatening infection to newborns and debilitated adults, are transmitted by the infusion of homologous leucocytes. Another life-threatening phenomenon affecting immunocompromised patients is Graft versus host disease (GVH); a disease in which the transfused leucocytes actually cause irreversible damage to the blood recipient's organs including the skin, gastrointestinal tract and neurological system. More recently, retroviruses such as HIV (AIDS) and HTLV1 have become a threat. Since some viruses, including several of those described above, are resident in the leucocytes, the removal of leucocytes is regarded as beneficial.

Conventional red cell transfusions have also been indicted as adversely influencing the survival of patients undergoing surgery for malignancy of the large intestine. It is believed that this adverse effect is mediated by the transfusion of agents other than donor red blood cells, including the donor's leucocytes.

Removal of leucocytes to sufficiently low levels to prevent the undesired reactions, particularly in packed red cells which have been derived from freshly drawn blood, is an objective of this invention.

In the currently used centrifugal methods for separating blood into the three basic fractions (packed red cells, platelet concentrate, and plasma), the leucocytes are present in substantial quantities in both the packed red cells and platelet concentrate fractions. It is now generally accepted that it would be highly desirable to reduce the leucocyte concentration of these blood components to as low a level as possible. While there is no firm criterion, it is generally accepted that many of the undesirable effects of transfusion would be reduced if the leucocyte content were reduced by a factor of about 100 or more prior to administration to the patient. This approximates reducing the total content of leucocytes in a single unit of PRC (the quantity of PRC obtained from a single blood donation) to less than about $1 \times 10^7$. Recently it has become more widely perceived that in order to prevent viral infection by transfused blood, factors of reduction should be more than 100, preferably more than 1000, and more preferably 30,000 or 100,000 fold or more, such as 1,000,000 fold.

One of the most effective means of reducing leucocyte content that has been discovered hitherto is disclosed in U.S. Pat. No. 4,925,572 (Application Ser. No. 07/259,773, filed Oct. 19, 1988), which is directed towards the bedside filtration of PRC. By contrast, this invention relates to the filtration of freshly drawn whole blood and of fresh PRC, that is, PRC that is filtered within 24 hours, and more preferably within 6 hours, of the time the blood was drawn. The behavior of fresh PRC is very different from that of the 2 to 35 day old blood that is described in U.S. Pat. No. 4,925,572. The standards for leucocyte depletion are also very different; the above copending application has as its objective leucocyte reduction by a factor of up to about 3000 to 10,000 and, while this is excellent for many purposes, the objective of the present application is leucocyte reduction by a factor in excess of about 30,000, and preferably of about 1,000,000 or more.

Defining a Unit of Blood and a Unit of Packed Red Cells

Blood banks in the United States commonly draw about 450 milliliters (ml) of blood from the donor into a bag which usually contains an anticoagulant to prevent the blood from clotting. Herein the quantity drawn during such a donation is defined as a unit of whole blood.

While whole blood is to a degree used as such, most units are processed individually by centrifugation to produce one unit of PRC. The volume of a unit of PRC varies considerably dependent on the hematocrit (percent by volume of red cells) of the drawn blood, which is usually in the range of about 37% to about 54%; and the hematocrit of the PRC, which varies over the range from about 50 to over about 80%, depending on whether yield of one or another blood compound is to be minimized. Most PRC units are in the range of about 170 to about 350 ml, but variation below and above these figures is not uncommon.

Drawn whole blood may alternatively be processed by separating the red cells from the plasma, and resuspending them in a physiological solution. A number of physiological solutions are in use. The red cells so processed may be stored for a longer period before use, and with some patients there may be some advantages in the removal of plasma. "Adsol" is the trade name of one such procedure, and SAG-M is a variant used in parts of Europe.

As used herein the term "fresh blood product" includes anti-coagulated whole blood, packed red cells obtained therefrom, and red cells separated from plasma and resuspended in physiological fluid, in all cases processed including filtration within about 24 hours and preferably within 6 hours of when the blood was drawn.

In parts of the world other than the United States, blood banks and hospitals may draw less or more than about 450 ml of blood; herein, however, a "unit" is always defined by the United States' practice, and a unit of PRC or of red cells in physiological fluid is the quantity derived from one unit of whole blood.

As used herein, PRC refers to the blood products described above, and to similar blood products obtained by other means and with similar properties.

Previously Available Means to Remove Leucocytes from PRC

The Spin-Filter system for obtaining leucocyte depleted packed red cells is described by Parravicini, Rebulla, Apuzzo, Wenz and Sirchia in Transfusion 1984; 24:508–510, and is compared with other methods by Wenz in CRC Critical Reviews in Clinical Laboratory Sciences 1986; 24:1–20. This method is convenient and relatively inexpensive to perform; it has been and continues to be used extensively. However, the efficiency of leucocyte removal, while generally about 90% or better, is not sufficiently high to prevent adverse reactions in some patients.

Centrifugation methods are available which produce lower levels of leucocytes in red cells, but these are laboratory procedures which are very costly to operate, and sterility of the product is compromised to a degree such that it must be used within 24 hours.

Other methods for leucocyte depletion, such as saline washing or deglycerolizing frozen red cells, have been or are used, but these have disadvantages for economical, high reliability service.

A number of devices have been proposed in which fibers are packed into housings, and whole blood passed through them in order to remove microaggregates and a portion of the leucocyte content. These devices have, when reduced to practice, all required saline to be applied either before or after use, or both before and after use, and are very poorly suited for blood bank use.

Characteristics Desirable in a Leucocyte Depletion Device

An ideal device for leucocyte depletion intended for use by blood banks would be inexpensive, relatively small, and be capable of processing one unit of PRC rapidly, for example in less than about one hour, and reduce the leucocyte content to the lowest possible level. Because of the high cost and limited availability of red blood cells, this ideal device would deliver the highest possible proportion of the red cells present in the donated blood. Such a device is an object of this invention.

Devices which have previously been developed in attempts to meet this objective have been based on the use of packed fibers, and have generally been referred to as filters. However, it would appear on preliminary review that processes utilizing filtration based on separation by size cannot succeed for two reasons. First, the various types of leucocytes range from granulocytes and macrocytes, which can be larger than about 15 μm, to lymphocytes, which are in the 5 to 7 μm range. Together, granulocytes and lymphocytes represent the major proportion of all of the leucocytes in normal blood. Red blood cells are about 7 μm in diameter, i.e., in size they are in the range of one of the two major components which must be removed. Secondly, all of these cells deform so as to pass through much smaller openings than their normal size. Accordingly, and because it is readily observed by microscopic examination that leucocytes are absorbed on a variety of surfaces, it has been widely accepted that removal of leucocytes is accomplished mainly by adsorption, rather than by filtration. An unexpected and surprising result of this invention, however, is that filtration through certain filters having a controlled pore size is critical to reach the target levels of leucocyte depletion.

Blood Component Recovery

In the preceding section, reference was made to the desirability of recovering a high proportion of the red cells delivered to the separation device. There are several causes for reduced recovery of red cells:

(a) Losses due to hold up within the connecting tubing;

(b) Losses due to liquid which remains within the device itself at the conclusion of the filtration;

(c) Losses due to adsorption on the surfaces of the device, or due to mechanical entrapment within the device;

(d) Loss due to clogging of the filter prior to completion of the passage of the full unit of blood; and (e) Losses due to contact with incompatible surfaces, which can cause clotting.

Capacity

As separated from whole blood in current blood banking practice, packed red cells contain not only a proportion of the leucocytes present in the blood as drawn from the donor, but also some platelets (which tend to be very adhesive), fibrinogen, fibrin strands, tiny fat globules, and numerous other components normally present in small proportions. Also contained are factors added at the time the blood is drawn to prevent clotting, and nutrients which help to preserve the red cells during storage.

During the centrifuging process which concentrates the red cells and partially separates them from the remaining components there is a tendency for microaggregates to form in PRC. These may comprise some red cells together with leucocytes, platelets, fibrinogen, fibrin, fat, and other components. Gels, which may be formed by fibrinogen and/or fibrin, may also be present in PRC produced by blood banks.

If the leucocyte depletion device comprises a porous structure, microaggregates, gels and occasionally fat globules tend to collect on or within the pores, causing blockage which inhibits flow.

Ease and Rapidity of Priming

Ease of use is an important characteristic of any leucocyte depletion system. As noted above, for leucocyte depletion devices, ease of priming is a particularly important factor. The term "priming time" refers to start-up of flow of PRC from the bag through the filter to the patient, and is the time required to fill the filter housing from its inlet to its outlet.

An object of this invention is to maintain a short priming time, preferably less than about 30 to about 120 seconds, to conserve technician time.

Preconditioning of Leucocyte Depletion Devices Prior to Priming

A number of devices in current use require pretreatment prior to passing blood, usually consisting of passing physiological saline. The necessity for such an operation is very undesirable in blood bank processing because it complicates the procedure, requires technician time, and puts maintenance of sterility at risk.

The reasons for using such pretreatment vary. They include removal of acid hydrolysate developed during steam sterilization of devices containing cellulose acetate fibers, assurance of freedom from foreign solids which may be present in natural fibers, and if the fibers are hygroscopic to prevent hemolysis (loss of the integrity of red blood cells with subsequent loss of their contents to the external milieu).

An objective of this invention is a leucocyte depletion device which requires no preconditioning prior to processing PRC derived from freshly drawn blood.

Definition of Voids Volumes

The concept of "voids volume" is related to, but distinguishable from, the term "bulk density". In fact, the term bulk density is misleading when referring to a broad spectrum of fibers with large variations in specific gravity. For example, polyester fibers may have a specific gravity of about 1.38 while inorganic fibers prepared from zirconia may have a specific gravity of greater than 5. Thus, in carrying out the instant invention, references to voids volume should not be confused with the term bulk density.

The concept of voids volume may be explained as follows.

Calculation of Voids Volume, Given Bulk Density and Fiber Density

Bulk density, D, is the weight of a given volume of fibrous aggregate divided by its apparent volume. Normally this is expressed in g/cc.

By fibrous aggregate is meant one or more fibers occupying a given or apparent volume, e.g., a mass of non-woven intertangled fibers with a certain proportion of voids or spaces within the mass.

In order to calculate the voids volume, V, the density, d, of the fibers must be known. The density, d, is also expressed in g/cc.

1. The volume of 1 gram of fibrous aggregate=1/D
2. The volume of 1 gram of fibers=1/d
3. The voids volume, V, is the total aggregate volume less the fiber volume or $$\frac{1}{D} - \frac{1}{d}$$

EXAMPLE

Given:

Volume of fibrous aggregate=10 cc

Weight of aggregate=1 g

Density of the aggregate D=1/10=0.1 g/cc

Density of fiber d=1.38

Volume of 1 g of the fibers is $\frac{1}{1.38} = .725$ cc

Hence voids volume $= \frac{1}{D} - \frac{1}{d} = \frac{1}{0.1} - \frac{1}{1.38} = 10 - .725$
$= 9.275$ cc or, expressed as percent $V = \frac{9.275}{10} \times 100$
$= 92.75\%$ The following table illustrates the difference between specifying voids volume and density. As illustrated there, at constant density, a column of glass fibers (glass being much more dense than, e.g., polypropylene) has a voids volume of 94% versus only 83.3% for a column of polypropylene.

| D, Column density (g/cc) | Material of the fiber | Density of the fiber, (g/cc) | Voids Volume (%) |
|---|---|---|---|
| 0.15 | glass* | 2.5 | 94.0 |
| 0.15 | polyester | 1.38 | 89.1 |
| 0.15 | polypropylene | 0.9 | 83.3 |

*Glass varies in density from about 2.3 to about 2.7 g/cc. The 2.5 g/cc figure used here is in the mid range.

Definition of Pore Diameter

In the definition of various filter media, it will be necessary to use the term "pore diameter". This term as used herein is as determined by the modified OSU F2 test described below.

Wetting of Fibrous Media

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension of about 3 dynes/cm higher compared with the one preceding. A drop of each may then be placed on a porous surface and observed to determine whether it is absorbed quickly, or remains on the surface. For example, applying this technique to a 0.2 µm porous tetrafluoroethylene (PTFE) filter sheet, instant wetting is observed for a liquid with a surface tension of about 26 dynes/cm. However, the structure remains unwetted when a liquid with a surface tension of about 29 dynes/cm is applied.

Similar behavior is observed for porous media made using other synthetic resins, with the wet-unwet values dependent principally on the surface characteristics of the material from which the porous medium is made, and secondarily, on the pore size characteristics of the porous medium. For example, fibrous polyester, specifically polybutylene terephthalate (hereinafter "PBT") sheets which have pore diameters less than about 20 µm will be wetted by a liquid with a surface tension of about 50 dynes/cm, but will not be wetted by a liquid with a surface tension of about 54 dynes/cm.

In order to characterize this behavior of a porous medium, the term "critical wetting surface tension" (CWST) is defined as follows. The CWST of a porous medium may be determined by individually applying to its surface a series of liquids with surface tensions varying by about 2 to about 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's are, respectively, about 27.5 and about 52 dynes/cm.

In measuring CWST, a series of standard liquids for testing is prepared with surface tensions varying in a sequential manner by about 2 to about 4 dynes/cm. Ten drops of each of at least two of the sequential surface tension standard liquids are independently placed on representative portions of the porous medium and allowed to stand for 10 minutes. Observation is made after 10 minutes. Wetting is defined as absorption into or obvious wetting of the porous medium by at least nine of the ten drops within 10 minutes. Non-wetting is defined by non-absorption or non-wetting of at least nine of the ten drops in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST.

A number of alternative methods for contacting porous media with liquids of sequentially varying surface tension can be expected to suggest themselves to a person knowledgeable of physical chemistry after reading the description above. One such involves floating a specimen on the surfaces of liquids of sequentially varying surface tension values, and observing for wet-through of the liquid, or if the fiber used is more dense than water, observing for sinking or floating. Another means would clamp the test specimen in a suitable jig, followed by wetting with the test liquids while applying varying degrees of vacuum to the underside of the specimen.

Appropriate solutions with varying surface tension can be prepared in a variety of ways, however, those used in the development of the product described herein were:

| Solution or fluid | Surface Tension range, dynes/cm |
|---|---|
| Sodium hydroxide in water | 94–110 |
| Calcium chloride in water | 90–94 |
| Sodium nitrate in water | 75–87 |
| Pure water | 72.4 |
| Acetic acid in water | 38–69 |
| Ethanol in water | 22–35 |
| n-Hexane | 18.4 |
| FC77 (3M Corp.) | 15 |
| FC84 (3M Corp.) | 13 |

Wetting of Fibrous Media by Blood

In packed red cells, as well as in whole blood, the red cells are suspended in blood plasma, which has a surface tension of about 73 dynes/cm. Hence, if packed red cells or whole blood is placed in contact with a porous medium, spontaneous wetting will occur if the porous medium has a CWST of about 73 dynes/cm or higher.

Hematocrit is the percent by volume occupied by red cells. The hematocrit of packed red cells ranges from about 50 to above 80%. Thus, about 50 to over 80% of the volume of PRC consists of the red cells themselves and, for this reason, the surface characteristics of the red cells influence the wetting behavior of PRC. The surface tension has been measured and is given in the literature as 64.5 dynes/cm. ("Measurement of Surface Tensions of Blood Cells & Proteins", by A. W. Neumann et al., from Annals N.Y.A.S., 1983, pp. 276–297.) The lower surface tension of red cells affects the behavior of PRC, for example during priming of filters and during filtration, in ways which are not fully understood.

The benefits conferred by preconditioning fibers to CWST values higher than the natural CWST of PBT and other synthetic fibers include:

(a) An important aspect of this invention is the discovery that fibrous media treated to convert the fiber surfaces to a particular range of CWST perform better with respect to priming time, leucocyte depletion efficiency, and resistance to clogging than do fibrous media with CWST values outside of those ranges.

(b) Synthetic fiber media whose CWST values have been elevated by grafting have, when hot compressed, superior fiber-to-fiber bonding and are for this reason preferred for use in making the preformed elements used in this invention.

(c) Detrimental effects such as occasional clotting of blood associated with non-wetting as described in previous sections are avoided.

(d) Devices made using unmodified synthetic fibers are recommended to be flushed with saline prior to use. This operation is undesirable since it causes blood loss due to hold-up within the complex tubing arrangement required, adds to cost, operation time, and operation complexity, and increases the probability that sterility may be lost. The need for preflushing is obviated by raising the CWST to the values disclosed in this invention.

Description Of The Invention

In accordance with the subject invention, a device and a method for depleting the leucocyte content of a blood product are provided.

The invention comprises a device for the depletion of the leucocyte content of fresh blood products which comprises a fibrous leucocyte adsorption/filtration filter with a pore diameter of from about 0.5 to less than 3.6 µm and having a CWST of from 53 to about 80 dynes/cm.

One of the significant advantages of the device of the invention relates to the priming of the filter assembly (i.e., inducing sufficient flow of PRC to fill the housing), which is more complex and more difficult than would appear at first sight.

If the CWST of the fiber surface is too low, for example that of unmodified synthetic fiber, relatively higher pressure is required to force the PRC to flow through. More seriously, areas of the filter medium tend to remain unwetted, preventing flow of PRC. Further, clotting may occur, especially with finer, high surface area fibers and with older blood.

For reasons which are not well understood, filters which have CWST in excess of about 90 dynes/cm have been observed to have very long priming times, ranging to about 2 to about 5 minutes. It has further been learned, by trial and error, that it is advisable that the CWST be held within a range somewhat above the CWST of untreated polyester fiber (52 dynes/cm), for example, about 55 dynes/cm and higher, and below about 75 or 80 dynes/cm, and more preferably from about 60 to about 70 dynes/cm.

The filter element of the invention has a pore size of from about 0.5 to less than 3.6 µm, preferably from about 0.5 to about 3.5 µm, more preferably from about 0.5 to about 2 µm.

This in itself is surprising since such pore sizes are significantly smaller than the size of blood components such as red blood cells which nevertheless pass through. The preferred element is typically made using 2.6 μm average fiber diameter radiation grafted melt blown polybutylene terephthalate (PBT) web, which in a preferred form is hot compressed to a voids volume of about 60% to about 85% and preferably about 65% to about 84% and has a pore diameter of about 0.5 to about 2 μm. The fiber surfaces of the adsorption element are surface grafted to provide a CWST preferably in the range of about 60 to about 70 dynes/cm, such as from about 62 to about 68 dynes/cm. It may be protected from clogging by a gel prefilter and/or by a microaggregate prefilter, and its function is to reduce the leucocyte content by a factor of 30,000 or more while allowing red cells to pass freely.

In a preferred device the fibrous filter medium of the invention is preceded by one or two preformed elements. If a three element filter is used, the function of the first, (the gel prefilter), is to remove gels; that of the second, (the microaggregate filter), is primarily to remove microaggregates though it can also remove some leucocytes by adsorption and by filtration; and the function of the third, the filter medium of the invention (often called hereinafter the adsorption/filtration filter), is to remove leucocytes by adsorption and by filtration. If only two elements are used, the first may be a gel prefilter or a microaggregate filter, followed by the adsorption/filtration filter of the invention. Each of these three elements may comprise one or more separate or integral fibrous layers. The respective elements may differ in their CWSTs, voids volumes, pore sizes, and number of layers. Each element may comprise one or more preforms each containing a number of layers. The respective preforms within each element may also differ with respect to the preceding characteristics.

Significant and novel preferred features of this invention which contribute to achieving high efficiency and capacity for leucocyte removal, and minimize loss of blood within the apparatus include:

(a) Previously disclosed devices have used a relatively small cross sectional area perpendicular to the flow path, and are correspondingly longer with respect to the depth of their flow paths. The preferred devices in accordance with this invention are larger in cross sectional area perpendicular to the flow path and correspondingly shorter in depth of flow. This improvement in design helps to prevent clogging by PRC containing unusually high quantities of gels or microaggregates.

(b) In order to make the larger cross sectional area economic and practical and to obtain the required degree of prefiltration, the filter components used in accordance with this invention are preferably preformed prior to assembly to closely controlled dimension and density parameters so as to form, in whole or in part, integral elements, self-contained and independent of other elements until assembled into a device in accordance with the subject invention. By "integral element" is meant a unitary, complete structure having its own integrity and, as mentioned, self-contained and independent of the other integral elements until assembled.

Preforming eliminates the pressure on the inlet and outlet faces of the housing which are inherent in a packed fiber system. Preforming also permits one element, for example, the first stage prefilter of the assembled device, to be more or less compressible, yet have a lower or higher density than the one following it. This arrangement contributes to longer life in service.

Preforming makes it more practical to use larger cross sectional area leucocyte depletion devices which have longer life in service, coupled with at least equal and usually better leucocyte removal efficiency, equal or better red cell recovery, and less hold up, when compared with devices that use fibers or fibrous webs packed into a housing at assembly.

Devices have been proposed and some made which comprise various commercially made woven and non-woven fibrous media as prefilters, along with a more finely pored last stage consisting of non-woven fibrous mats, all packed within a plastic housing. These devices have not had the efficient prefiltration made possible by preforming and, in addition, have been prone to occasional clogging, being too small in cross sectional area.

(c) While it might be thought that freshly drawn blood would be free of aggregates and gels, hence prefiltration would not be required to prevent filter clogging, it has been the experience of the applicants that freshly drawn blood does occasionally clog a filter capable of producing a filtrate with less than about $10^4$ leucocytes per unit of PRC, corresponding to a reduction in leucocyte content by a factor of about $10^5$.

Because of the difficulty of predicting the consequences of the unusual and variable combination of clogging factors that may be present, even for a person skilled in the art of filter design, it is advisable to incorporate an efficient prefilter.

The present invention, therefore, provides for the optional use of an efficient, small volume gel prefilter system which will contribute to the objective of achieving an average reduction of leucocyte content by a factor of about 30,000 or more, while rarely or never clogging when passing one unit of packed red cells derived from freshly drawn blood.

The use of such an effective gel prefilter which consistently retains at least a substantial proportion of the gel content of one unit of PRC derived from freshly drawn blood is, therefore, a preferred feature of one aspect of this invention. This makes possible the use of a device with a smaller internal volume, with less blood loss due to internal hold-up, while consistently delivering one unit of PRC without clogging.

(d) While the gel prefilter is extremely efficient in removing gels with a very small increase in pressure drop, and frequently removes as well quantities of microaggregates suspended in the gels, it removes only a portion of any microaggregates that may be present. Removal of the smaller microaggregates may be accomplished by one, two, or more layers of prefiltration using filter media of intermediate pore diameter which may either be separate preformed layers, but which in a preferred form of this invention are integral with part or all of the adsorption/filtration element.

(e) The housing into which the element assembly is sealed is uniquely designed to achieve convenience of use, rapid priming, and efficient air clearance, this last leading to further reduction in hold-up of PRC.

(f) The lateral dimensions of the elements are larger than the corresponding inner dimensions of the housing into which they are assembled. For example, if the elements are of disc form, the disc outside diameter is made about 0.1 to about 0.5% larger than the housing inside diameter. This provides very effective sealing by forming an interference fit with no loss of effective area of the elements, and contributes further towards minimization of the blood hold-up volume of the assembly.

BEST MODE FOR CARRYING OUT THE INVENTION

Figure 1:
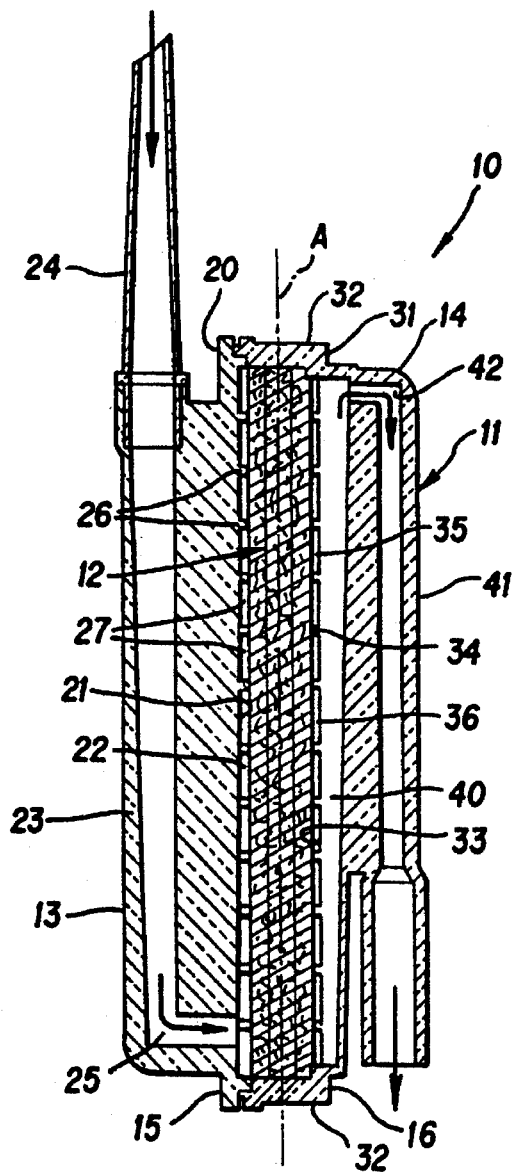
FIG. 1 is a cross sectional view of an exemplary depletion device employing the filter element of the present invention.
Figure 4:
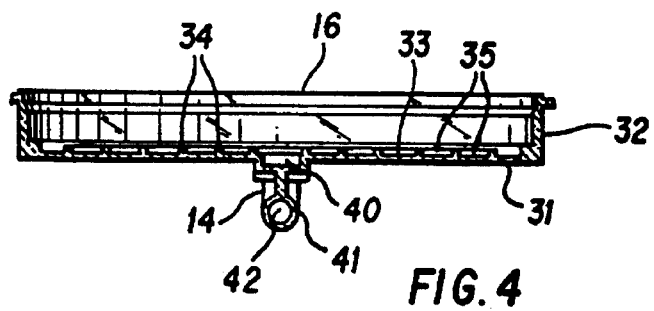
FIG. 4 is a cross sectional view of the outlet section shown in FIG. 3.

Material for Use in Construction of Leucocyte Removal Devices

A variety of starting materials other than fibers can be considered; for example, porous media could be cast from resin solution to make porous membranes, or sintered metal powder or fiber media could be used. However, considerations of cost, convenience, flexibility, and ease of fabrication and control, point to fibers as a preferred starting material.

In order to achieve good priming with the fibrous medium fully wetted and in the absence of surfactant deliberately added to reduce the surface tension of the blood product, it would appear at first glance from elementary consideration of the physical chemistry involved that blood component devices should be made of materials which have CWST values in the range of about 70 to about 75 dynes/cm or higher. Practical considerations dictate the use of commercially available fibers. Synthetic resins from which fibers are prepared commercially include polyvinylidene fluoride, polyethylene, polypropylene, cellulose acetate, Nylon 6 and 66, polyester, polyacrylonitrile, and polyaramid. An important characteristic of resins is their critical surface tension (Zisman, "Contact angles, wettability and adhesion", *Adv. Chem. Ser.* 43, 1–51, 1964). These resins have critical surface tensions ($\gamma_c$) ranging from about 25 to about 45 dynes/cm. Experience has shown that the CWST of filters in the pore sizes preferred in the products of this invention can be expected to be less than about 10 dynes/cm higher than $\gamma_c$. For example, for polytetrafluoroethylene, $\gamma_c$ is 18 and CWST is 27.5, while for a polyester PBT fibrous mat, $\gamma_c$ is 45, and CWST is 52. No commercially available synthetic fiber has been found which has a CWST higher than about 52 dynes/cm.

Some natural fibers have CWST greater than 52, but natural fibers smaller than about 15 μm in diameter are not generally commercially available. Synthetic fiber webs in which the fibers are less than about 5 μm in diameter can be made by the melt blowing process, and compared with natural fibers, such fibers require one third or less the mass to provide equal fiber surface area for adsorption of leucocytes, and consequently, occupy less volume when fabricated into filters of a given pore diameter. For this reason, natural fibers are less suited for manufacturing leucocyte removal devices with optimally low hold-up volume. For example, a commercially available packed cotton fiber device currently used for leucocyte depletion has a priming volume of over 75 ml, which is more than twice the volume of the preferred device described in this application. Furthermore, the makers of this device require saline to be passed before and after the PRC has been passed, and the device is not suitable for bedside use. Additionally, blood so processed must be used within 24 hours.

The art of surface grafting has been the subject of extensive research for 25 years or more. Numerous publications in the scientific literature and a large number of patents describe a variety of methods and procedures for accomplishing surface modification by this means. One such method employs monomers comprising an acrylic moiety together with a second group which can be selected to vary from hydrophilic (e.g., —COOH or —OH) to hydrophobic (e.g., saturated chains such as —CH$_2$CH$_2$CH$_3$), and these have been used in the process of this invention. Heat, UV, and other reaction energizing methods can be used to initiate and complete the reaction. However, cobalt source radiation grafting has been selected as most convenient and has been used in this invention to modify the CWST of fibrous mats. By cut and try selection, mixtures of monomers or single monomers can be found which will produce a fibrous mat of polybutylene terephthalate in which the CWST has been increased from 52 to any desired value up to as high as is possible to be measured by the method described above. The upper limit is set by the paucity of liquids with surface tensions at room temperature higher than about 110 dynes/cm.

During the development of this invention, devices were prepared using media in which grafting was accomplished by compounds containing an ethylenically unsaturated group such as an acrylic moiety combined with a hydroxyl group (for example, 2-hydroxyethyl methacrylate, or "HEMA"). A second acrylic monomer, such as methyl acrylate (MA) or methyl methacrylate (MMA), which tend to cause the grafted porous webs to have lower CWST, can be used in combination with HEMA, and by varying the proportions, any CWST between about 35 to about 45 to over 110 dynes per cm can be obtained.

Liquids with surface tensions lower than the CWST of the porous medium will wet the medium and, if the medium has through pores, will flow through it readily. Liquids with surface tensions higher than the CWST will not flow at all at low differential pressures, but will do so if the pressure is raised sufficiently. If the surface tension of the liquid is only slightly above the CWST, the required pressure will be small. If the surface tension differential is high, the pressure required to induce flow will be higher.

It has been discovered that, when a liquid is forced under pressure to pass through a fibrous mat which has a CWST more than about 15 to about 20 dynes/cm lower than the liquid's surface tension, flow tends to occur in a non-uniform fashion, such that some areas of the mat remain dry. This is highly undesirable in a leucocyte depletion device, first because the pressure drop is higher causing earlier clogging, second because all the flow passes through only a portion of the available area, again increasing the probability of clogging, and third because only a portion of the fiber surface area available for adsorption of or retention by filtration of leucocytes is used for that purpose and, as a result, leucocyte removal is less efficient.

Solutions to the Problems of Poor Wetting of Synthetic Fibers

Fiber surface characteristics of most or all of the synthetic resins listed above, as well as of other materials, can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, or to various other forms of radiation, among which gamma-radiation is particularly useful.

As examples of these various methods, stainless steel fibers can be made water wettable, i.e., provided with a $\gamma_c$ greater than about 72 dynes/cm by oxidation in air at about 370° C. to produce a thin oxide surface skin. Synthetic organic and glass fibers may be coated by polymers which contain at one end a reactive (e.g., epoxide) moiety and at the other a hydrophilic group.

While the above methods and others known to those familiar with surface modification techniques can be used, radiation grafting, when carried out under appropriate conditions, has the advantage that considerable flexibility is available in the kinds of surfaces that can be modified, in the wide range of reactants available for modification, and in the systems available for activating the required reaction. In the subject invention gamma-radiation grafting has been focused on because of the ability to prepare synthetic organic fibrous media with CWST over the full range of from below about 50 to above 80 dynes/cm. The products are very stable, have zero or near zero aqueous extractables levels and, in addition, improved adhesion between fibers is obtained when used in preformed prefiltration or in adsorption/filtration elements.

Selection of Fiber Diameter for Use in Leucocyte Depletion Devices

As noted in the section headed "Characteristics Desirable in a Leucocyte Depletion Device", adsorption of leucocytes on fiber surfaces is widely accepted as the mechanism of leucocyte removal. Since the surface area of a given weight of fibers is inversely proportional to the diameter of the fibers, and removal of leucocytes by adsorption to the fiber surfaces is a significant mechanism for leucocyte depletion, it is to be expected that finer fibers will have higher capacity and that the quantity, as measured by weight of fibers necessary to achieve a desired efficiency, will be less if the fibers used are smaller in diameter.

For this reason and because it is well known that finer fibers quite generally contribute to higher efficiency and longer life of filters, the trend has been to use finer fibers for leucocyte depletion. Historically, as the technology required to produce smaller diameter fibers has advanced, they have soon thereafter been packed into housings and/or proposed to be used for leucocyte depletion.

Selection of Fiber for Leucocyte Depletion Devices

A number of commonly used fibers, including polyesters, polyamides, and acrylics, lend themselves to radiation grafting because they have adequate resistance to degradation by gamma-radiation at the levels required for grafting, and they contain groups with which available monomers can react. Others, such as polypropylene, are less readily adapted to modification by grafting.

As noted above, fiber diameters should be as small as possible. Synthetic fibers made by conventional spinneret extrusion and drawing are not currently available smaller than about 6 μm in diameter.

Melt blowing, in which molten resin is attenuated into fibers by a high velocity stream of gas and collected as a non-woven web, came into production in the 1960s and 1970s and has been gradually extended over the years with respect to the lower limit of fiber diameter with which webs could be made. Within recent years, webs with fiber diameters less than 3 μm have been achieved, and more recently, webs of good quality with average fiber diameter less than 2 μm have been made.

Some resins are better adapted to melt blowing of fine fibers than are others. Resins which work well include polypropylene, polymethylpentene, polyamides such as Nylon 6 and Nylon 66, polyester PET (polyethylene terephthalate), and polyester PBT (polybutylene terephthalate). Others may exist that have not yet been tested. Of the above listed resins, polyester PBT is a preferred material because it lends itself to radiation grafting and to subsequent conversion into preformed elements of controlled pore size by hot pressing.

Polyester PBT has been the principal resin used for the development of the products of this invention and is, except for a portion of a gel prefilter, the resin used in the examples. It should be noted, however, that other resins may be found which can be fiberized and collected as mats or webs with fibers as small as about 1.5 μm in diameter or less, and that such products, with their CWST adjusted if necessary to the optimum range, may be well suited to the fabrication of equally efficient but still smaller leucocyte depletion devices. Similarly, glass and other fibers, appropriately treated, may make suitable devices with very low hold-up of blood.

Description of an Exemplary Depletion Device

As shown in FIGS. 1–4, an exemplary depletion device 10 generally comprises a housing 11 and a separation element or filter-adsorber assembly 12. The housing 11 has an inlet 13 and an outlet 14 and defines a fluid flowpath between the inlet 13 and the outlet 14. The filter-adsorber assembly 12 is disposed within the housing 11 across the fluid flowpath and serves to separate undesirable substances, such as gels, fat globules, aggregates, and leucocytes, from a fluid, such as a suspension of packed red cells, flowing through the housing 11.

Housings can be designed to accept a variety of shapes of filter-adsorber assemblies. One such is, for example, a square. Those and other possible forms would in principle all be functional, provided that adequate flow area is provided.

A square filter-adsorber assembly would in theory allow more economical use of material, but would be less reliable if an interference fit seal were used in the manner described below for housings fitted with disc shaped filter-adsorber assemblies. If sealing is obtained by edge compression about the periphery, significant effective area is lost at the seal. For those reasons, cylindrical housings with disc shaped filter-adsorber assemblies assembled with an interference fit seal are preferred, although other forms may be used. Circular housings with an effective cross sectional area of about 62 $cm^2$ have been used in developing this invention.

Housings can be fabricated from any suitably impervious material, including an impervious thermoplastic material. For example, the housing may preferably be fabricated from a transparent polymer, such as an acrylic or polycarbonate resin, by injection molding. Not only is such a housing easily and economically fabricated, but it also allows observation of the passage of the fluid through the housing. The housings are designed to withstand normal abuse during service, as well as internal pressures up to about 3 psi (0.2 $Kg/cm^2$). This permits light construction, which is a desirable feature of this invention made possible by the use of preformed filter-adsorber assemblies. The force required to compress the fibers of an efficiently designed filter-adsorber assembly by packing of fibers into a housing is as high as about 68 kilograms for a 62 $cm^2$ disc, or about 1.1 $kg/cm^2$, requiring heavier, bulkier, and more costly housing construction.

While the housing may be fashioned in a variety of configurations, the housing 11 of the exemplary separation device 10 is preferably fashioned in two sections, i.e., an inlet section 15 and an outlet section 16. The inlet section 15 includes a circular inlet plate 20, and the inside surface of the circular inlet plate 20 defines a wall 21 which faces the upstream surface of the filter-adsorber assembly 12.

Figure 2:
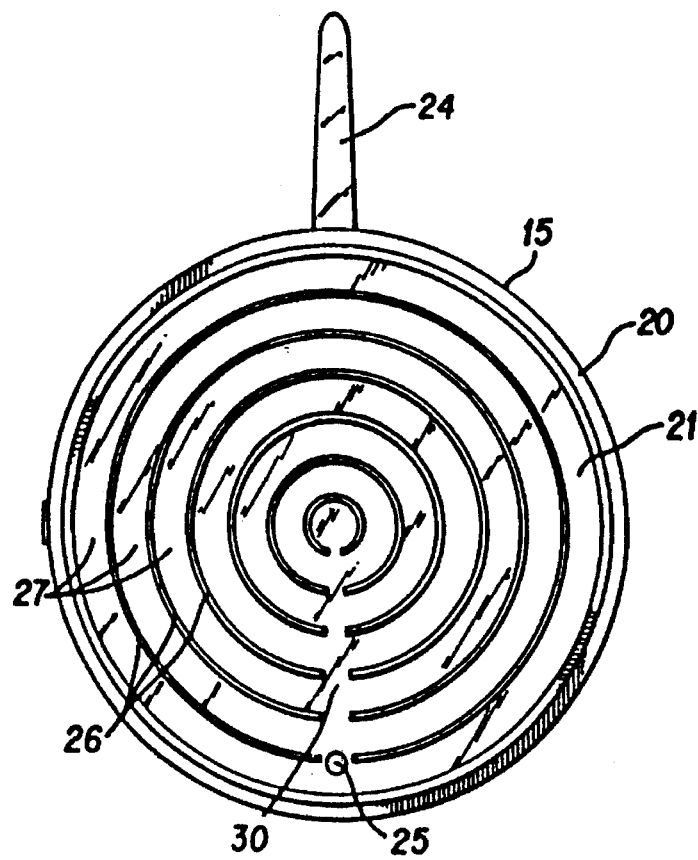
FIG. 2 is an elevation view of the inside surface of the inlet section of the depletion device shown in FIG. 1.
Figure 3:
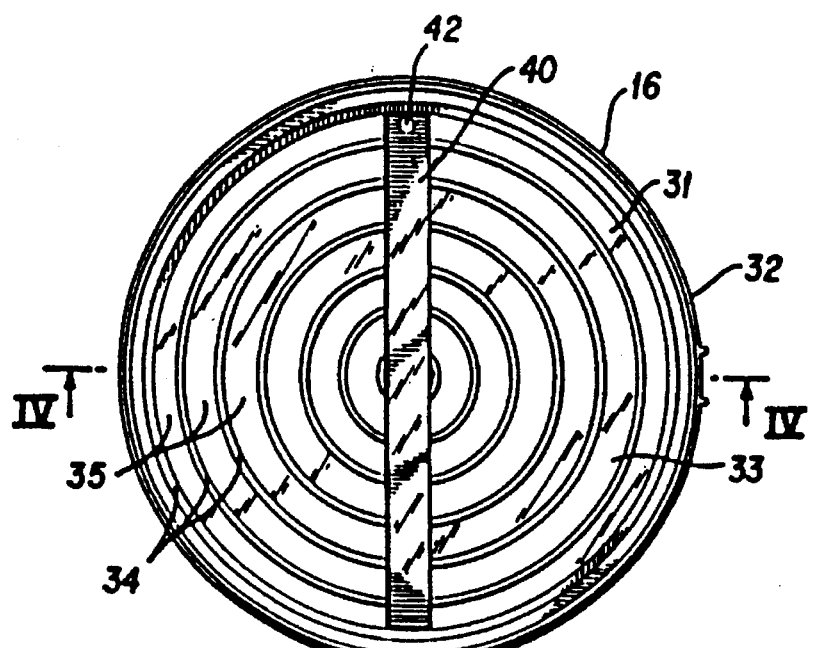
FIG. 3 is an elevation view of the inside surface of the outlet section of the depletion device shown in FIG. 1.

The inlet 13 delivers the fluid to an inlet plenum 22 between the wall 21 and the upstream surface of the filter-adsorber assembly 12. In accordance with one aspect of the invention, the inlet 13 delivers the fluid to the inlet plenum 22 at or near the bottom of the housing 11, as shown in FIGS. 1 and 2.

The inlet may be variously configured. However, the inlet 13 of the exemplary separation device 10 includes a longitudinal inlet ridge 23. The inlet ridge 23 extends along the outside surface of the circular inlet plate 20 parallel to a diametrical axis A of the housing 11, which, in use, is positioned with the diametrical axis A oriented generally vertically. The upper end of the inlet ridge 23 may be fashioned as a socket for receiving a hollow spike 24 which is used to pierce the bottom of a bag containing the fluid, e.g., a blood bag. The inlet 13 further includes an inlet passageway 25 which opens at the upper end of the hollow spike 24, extends through the hollow spike 24 and the inlet ridge 23, and communicates with the inlet plenum 22 at the bottom of the inlet section 15.

The wall 21 of the circular inlet plate 20 includes a plurality of generally concentric circular ridges 26 which define concentric circular grooves 27. The ridges 26 abut the upstream surface of the filter-adsorber assembly 12. As shown in FIG. 2, the ridges 26 terminate in the lower portion of the inlet section 15, defining a passageway or access 30. The access 30 extends between the inlet passageway 25 and each circular groove 27, allowing fluid to flow from the inlet passageway 25 to the circular grooves 27. Collectively, the circular grooves 27 and the access 30 define the inlet plenum 22, which distributes the fluid delivered by the inlet passageway 25 over the whole upstream surface of the filter-adsorber assembly 12. To prevent aggregates and other large obstructions from blocking flow at or near the junction of the inlet passageway 25 and the inlet plenum 22 and, at the same time, to minimize hold-up volume in the housing 11, the depth of the inlet plenum 22 is greatest at the bottom of the housing 11 and decreases along the vertical axis A to a minimum value at the horizontal centerline of the housing 11.

The outlet section 16 of the housing 11 includes a circular outlet plate 31 and a cylindrical collar 32 which extends from the periphery of the circular outlet plate 31 to the periphery of the circular inlet plate 20. The cylindrical collar 32 is preferably integrally formed with the circular outlet plate 31 and joined to the circular inlet plate 20 in any suitable manner, e.g., by an adhesive or by sonic welding.

The inside surface of the circular outlet plate 31 defines a wall 33 which faces the downstream surface of the filter-adsorber assembly 12. The wall 33 includes a plurality of generally concentric circular ridges 34 which define concentric circular grooves 35. The ridges 34 abut the downstream surface of the filter-adsorber assembly 12. The circular grooves 35 collectively define an outlet plenum 36 which collects the fluid passing through the filter-adsorber assembly 12. The depth of the outlet plenum 36 is made as small as possible to minimize hold-up volume within the housing 11 without unduly restricting fluid flow.

In accordance with another aspect of the invention, the wall 33 further includes a passageway such as a slot 40 which communicates with the outlet 14 at or near the top of the outlet section 16. The slot 40, which collects fluid from each of the circular grooves 35 and channels the fluid to the outlet 14, preferably extends from the bottom to the top of the outlet section 16 along the vertical axis A. In the exemplary separation device 10, the width of the slot 40 remains constant but the depth of the slot 40, which is greater than the depth of the outlet plenum 36, increases from the bottom to the top of the outlet section 16 along the vertical axis A. Alternatively, the height may be less than the diameter of the housing, the width may vary, or the depth may remain constant. For example, the slot may extend from the top of the housing along the vertical axis A a distance in the range from about 80% of the inside diameter of the housing.

The outlet 14 may be variously configured. However, the outlet 14 of the exemplary depletion device 10 includes a longitudinal outlet ridge 41 which extends along the outside surface of the outlet plate 31 parallel to the vertical axis A. The lower end of the outlet ridge 41 may be fashioned as a tubing connector or as a socket for receiving a tubing connector or other apparatus. The outlet 14 further includes an outlet passageway 42 which communicates with the slot 40 at or near the top of the housing 11, extends through the outlet ridge 41, and opens at the lower end of the outlet ridge 41.

As blood starts to flow through the apparatus, filling it from the bottom and emptying at the top, air is displaced and flows towards and out of outlet passageway 42. By careful design of the exemplary apparatus it has been possible to reduce, but not to eliminate completely, the situation in which some liquid reaches the area adjacent to the outlet passageway 42 before all of the air is cleared from the inner parts of the housing assembly. In the absence of slot 40, this lagging air flow would carry some red cell-containing suspension into the outlet passageway 42. Slot 40 allows the blood so carried to flow into the slot, where the air is harmlessly separated from the liquid suspension. The air then rises harmlessly to the outlet 14 ahead of the rising fluid level in the slot 40 and is almost completely ejected before the liquid level reaches the top of the outlet plenum 36 and outlet passageway 42. Thus, air is very efficiently cleared from the housing 11 of the exemplary depletion device 10 according to the invention. For example, in a depletion device which has an inside diameter of about 8.9 cm, an initial air volume of 36 cc, and a slot about 8 cm high, about 0.73 cm wide, about 0.2 cm deep at the bottom, and 0.33 cm deep at the top, the residual volume of air passing through the outlet after 1 or 2 cc of blood has passed through the outlet is estimated to be less than about 0.1 cc.

In order to understand the importance of the slot and the flow passage configuration, the equivalent operation of a conventional leucocyte depletion unit will be described.

In conventional units, fluid enters at the top of the housing and exits at the bottom. The housing of such a unit is typically connected by plastic tubing between a blood bag upstream from the conventional housing and a transparent drip chamber downstream from the conventional housing and thence to the patient. During priming, the housing along with the drip chamber is inverted and blood is forced through the conventional housing into the drip chamber. This has the disadvantage that some pressure head is lost, but, more seriously, fluid reaches the exit of the conventional housing and enters the drip chamber while as much as 1 to 2 cc or more of air is still trapped in the conventional housing. Blood bank practice requires that the volume of air delivered to the collection bag be kept to the lowest possible value, even 1 or 2 cc being undesirable.

The filter-adsorber assembly 12 preferably comprises a number of individually preformed layers as described below under the heading "Fabrication of Fibrous Elements." During the development stage, housings were constructed for testing which incorporated the basic internal configuration described above, but in addition were variable with respect to the thickness of the filter-adsorber assembly. In this way, it was possible to test filter-adsorber assemblies varying in total thickness. In each case, the distance between the tips of the ridges 26, 34 of the inlet and outlet sections was adjusted to be equal to the nominal total thickness of the filter-adsorber assembly.

To provide an interference fit of the filter-adsorber assembly 12 within the housing 11, the filter-adsorber elements were cut from large precompressed slabs to a diameter about 0.1 to about 0.5% larger than the inside diameter of the cylindrical collar 32. The filter-adsorber elements were cut in such a manner as to maintain true right cylindrical form at their outer edges. This, coupled with the slight oversizing, provides good edge sealing, i.e., an interference fit, between the outer edges of the filter-adsorber assembly 12, made up of the various filter-adsorber elements, and the inner periphery of the housing 11.

Fabrication of a Gel Prefilter Element

A first element of those assembled into the above described housing is referred to as a gel prefilter. A proportion of PRC specimens contain gels, fat globules, or microaggregates which can clog filter media. The gels form a phase distinct from, and not miscible with, the blood plasma in which they are suspended. The state-of-the-art procedure for coping with clogging of filters is enlargement of the pore openings of the upstream layer or layers, continuously or in relatively small steps, but this procedure is inefficient when applied to the device of this invention, as a significant number of graduated pore size layers are required, and these tend to occupy a relatively large volume, and for this reason would cause an excessive volume of blood to be held up within the device. Whereas the normal means calls for uniformly graduated pore size, continuously or in relatively small steps, the pore diameter of the preferred products of this invention change abruptly, by a factor of about ten, in the transition from the gel prefilter (first element) to the immediately adjacent microaggregate filter (second element), thereby accomplishing a substantial reduction in the overall volume of the filter element.

Needle punched webs are made using staple fibers, which for synthetic fibers are usually derived from continuous filament by cutting or tearing the filament into lengths of usually about 3 to 6 cm. These straight lengths are laid onto a moving belt after suspending them in air, and the fibers are interlaced by reciprocating multi-barbed needles.

The fibers assume the form of irregular loops, circles, and spirals, interspersed with a variety of other irregular shapes. Straight sections are few, and fewer sections still are straight for more than a fraction of a millimeter. A notable characteristic is that at least about 90% of the fibers depart for at least one portion of their length from the planar structure which characterizes other non-wovens, i.e., significant portions of the fibers of needle punched media are not parallel to the plane of the web. Gels appear to penetrate easily into this type of web, but to be effectively retained within the web, as may be seen by post-test microscopic examination.

The structure of needle punched webs is in strong contrast with respect to fiber orientation when compared with non-wovens such as melt blown web, in which the fibers are essentially parallel to the plane of the web.

Needle punched webs are generally thicker as made than is desired for gel removal, and for optimal use are hot compressed to a controlled smaller thickness. Fabric so made was discovered to be particularly effective in retaining gels. Further, such fabrics can be nearly filled with collected gel, yet allow free flow of blood to the downstream component of the system.

While the gel prefilter does not recover microaggregates directly by filtration, the gels it retains may contain microaggregates, and these are efficiently retained along with the gels.

The "type A" gel prefilters used in the examples of this invention comprise a needle punched web made using polyester PET fibers of average diameter about 23 µm, bonded by polyethylene isoterephthalate. Nominal weight is about 0.008 g/cm$^2$. The fiber lubricant is removed using a hot solution of trisodium phosphate and detergent, and the web then thoroughly washed and dried prior to use.

A needle punched web identical with the web described above was used as one of the components of the gel prefilter of U.S. Pat. No. 4,925,572. For use with PRC derived from freshly drawn blood which has relatively fewer gels and microaggregates, the same prefilter has been used, but compressed to a smaller thickness, as described below.

Other gel prefilters that can be used in the devices of this invention include melt blown fibrous webs, particularly those having fiber diameters of from about 10 to about 30 µm, and preferably those with fiber diameters of about 20 µm.

Fabrication of Preferred Microaggregate Filter

In U.S. Pat. No. 4,925,572, three layers of prefiltration are described. For use with fresh PRC, fewer prefiltration layers can be used, or indeed none at all need be used, with little or no risk of clogging. Among the Examples in accordance with this invention, we have used as the microaggregate filter a 6.5 mg/cm$^2$ layer of web of fiber diameter 3.2 µm followed by a 6.9 mg/cm$^2$ layer of web of fiber diameter 2.9 µm in diameter. These are compressed to a voids volume of about 74% to about 84%. The fibers of both these layers are surface grafted to provide a CWST in the range of about 60 to about 70 dynes/cm.

Fabrication of an Adsorption/Filtration Element

Leukocytes are removed to only a small degree by the gel prefilter and microaggregate filter. The principal contributor to leukocyte removal is the adsorption/filtration element, which comprises preferably one or more hot compressed preforms of multiple identical layers of relatively small fiber diameter melt blown web.

Preforming and Assembly of the Elements

In a preferred filter of the invention, flow through the above elements is in the order in which they are listed, that is, gel prefilter, microaggregate filter, and then the adsorption/filtration element. The gel prefilter preferably comprises about two to four layers, the microaggregate prefilter comprises preferably one to four layers, and the adsorption/filtration element generally comprises one or more preforms, each comprising a number of layers. In a more preferred embodiment, the adsorption/filtration element comprises two sets of multi-layers, each comprising a different voids volume. Multilayers may be preferred for the adsorption/ filtration element because the melt blowing process is such that making a single layer of the weight, thickness, fiber diameter and uniformity required is difficult.

These multiple layers can be used as individual preformed layers assembled in the order noted, however, it is sometimes more convenient to fabricate them as subassemblies. In one preferred configuration of the gel prefilter, two layers of needle punched medium and one of melt blown medium are hot compressed together into a single preform, while in another two or more precompressed layers of melt blown web are used as separate layers.

The values cited above and in the examples can be varied within limits while meeting the objective of this invention. To determine whether any particular variation produces a fully equivalent product, tests are required. Thus, it should be understood that, while the precise materials, fiber diameters, weights, densities, thicknesses and number of layers can be varied somewhat while achieving equivalent or possibly even better results, that which is disclosed herein is intended as a guide to the design of a device meeting the stated objectives of this invention and that devices made with such variations fall within the scope of this invention.

With the exception of the gel prefilter, all of the elements are preferably surface treated to a CWST in excess of about 55 dynes/cm, but not in excess of about 75 to about 80 dynes/cm, and more preferably from about 60 to about 70 dynes/cm.

Hot compressed element preforms made using melt blown fibrous mats which have been surface modified to raise their CWST values by 5 or more dynes/cm are palpably better with respect to firmness and resistance to fraying when compared with discs made by hot compression followed by radiation grafting. Grafting prior to hot compression is for this reason preferred; however, serviceable elements could be made by hot compression followed by grafting.

While the examples of this invention have used hot compression to form the integral elements which together combine to provide prefiltration, gel removal, and adsorption, it would be feasible to form the integral elements by other means, such as resin bonding, and a device utilizing this or similar alternatives is within the scope of this invention.

Melt blown fibers have been preferred for use in all but the first layer of these devices. Should finer melt blown or other fine fibers, for example, fibers made by mechanical fibrillation of larger diameter fibers or by other means, become available in the future, their use in elements for leucocyte depletion devices would be within the scope of this invention.

Edge Sealing the Preformed Elements into the Housing

The housing is preferred to be of generally disc form, or more rigorously stated, in part have the form of a right cylinder. The preformed elements are made also in right cylindrical form, of dimension about 0.1 to about 0.5% larger in diameter than that of the inner surface of the housing. When assembled, a good seal is obtained, with no detectable bypassing during service.

In order to achieve good sealing, circular elements must have a truly right cylindrical form. That form is not achieved by all the means by which the elements can be cut to circular form; for example, an obvious means, stamping out a circle using a steel rule die, does not provide an acceptable outer seal. Instead, the disc must be cut to its finished diameter using means which achieve the geometry of a true right cylinder at the cut edges. This has been achieved in the practice of this invention by construction of a circular knife of the required diameter, which is rotated to cut a true right cylinder while holding gently but firmly in place the inner and outer surfaces of the precompressed slab from which the disc is cut.

Circular housings may be adapted to a procedure in which a bag containing the collected PRC is attached to the filter aseptically, followed by application of pressure to the bag containing the PRC to force the PRC through the filter into a second collection bag.

In an alternate procedure the filter and a second PRC collection bag are provided as part of the blood collection set prior to attaching the set to the blood donor. When this procedure is used, the blood is drawn into the first collection bag, that bag along with the filter and the auxiliary bags are placed into the centrifuge bucket, following which the assembly is spun to make the PRC. For use in this procedure it is desirable for reasons of economy to use as small as possible a bucket. In order to make this possible, it may be preferred that the filter have a form other than circular, for example, rectangular. Rectangular filters can be sealed by an interference fit at their outer edge into a rectangular housing, however, they may in addition or alternately be preferred to have a peripheral compression seal.

CWST of the Elements

The gel prefilter (first) element may have a low CWST without harm, and indeed may function better in that condition. The results of tests in which sufficient PRC is run through a device to cause clogging or near clogging, followed by dissection, inspection, and testing of the pressure drops of the individual layers, indicate that little if any improvement can be accomplished by increasing the CWST of this layer. The microaggregate filter element and the adsorption/filtration element are preferably modified to a CWST of between about 55 to about 80 dynes/cm, and more preferably to between about 60 and about 70 dynes/cm, and still more preferably to between about 62 and about 68 dynes/cm.

Red Cell Recovery

No significant changes in hematocrit were detected when the hematocrit values for the blood in the bag were compared with the effluent from the devices in accordance with this invention.

Some of the incoming blood or PRC is lost due to hold-up within the depletion device. That loss is reported as blood hold-up volume.

Characterization of Porous Media by Physical Characteristics

Formulae have been proposed to predict pore diameter. These formulae typically use fiber diameter, for example as determined by BET testing; bulk (apparent) density; and fiber density. One such, for example, calculates the average distance between fibers. However, the average distance between fibers can not be a meaningful predictor of performance as in any liquid flow path it is the largest pore or pores encountered which control performances, and this is particularly true of deformable "particles" such as leucocytes. In a fibrous mat such as made by melt blowing, the fibers are laid down in a random manner, and the pore size distribution is quite wide. Other means for forming fibrous mats, e.g., air laying, or formation on a Fourdrinier screen, also produce wide pore size distributions. In these circumstances, the average distance between fibers is clearly a poor predictor of performance. A variety of other formulae have been proposed to allow calculation of pore diameters from data on fiber diameter, fiber density and bulk density, but applicants are unaware of any formula that has proved useful for calculating a priori the effective pore diameter of filters for liquid service.

Measurement of fiber surface area, for example by gas adsorption—popularly referred to as "BET" measurement—is a useful technique, as the surface area is a direct indication of the extent of fiber surface available to remove leucocytes by adsorption. In addition, the surface area of melt blown PBT webs can be used to calculate fiber diameter. Using PBT, of density 1.38 g/cc as an example:

$$\text{Total volume of fiber in gram} = \frac{1}{1.38} \text{ cc, and}$$

this volume is equal to the fiber cross sectional area multiplied by its length, hence $$\frac{\pi d^2 L}{4} = \frac{1}{1.38} \quad (1)$$

Surface area of the fiber is $\pi dL = A_f$ (2)

Dividing (1) by (2) $\frac{d}{4} = \frac{1}{1.38 A_f}$ and $$d = \frac{4}{1.38 A_f} = \frac{2.9}{A_f} \text{ or } (0.345 A_f)^{-1}$$

where L=total length of fiber per gram, d=average fiber diameter in centimeters, and $A_f$=fiber surface area in cm²/g.

If the units of d are μm, the units of $A_f$ become square meters/gram (M²/g), which will be used hereinafter. For fibers other than PBT, their density is substituted for that of PBT.

A second characteristic necessary to describe a porous medium adequately to permit it to be reproduced is its pore diameter (Dp). We have used a modified OSU-F2 test for this purpose; this test and its mode of use are described in the following section.

Other characteristics which describe a porous medium include apparent (bulk) density (ρ) in grams/cubic centimeter (g/cc), the fiber density (also in g/cc), the thickness (t) of the elements of the medium, specified in centimeters (cm), the cross sectional area available for flow through the filtering element in square centimeters (62 cm² for all of the examples), and the CWST in dynes/cm. Specifying these parameters defines a filter or filter-adsorber element of predictable behavior when used for leucocyte depletion.

Processing Blood Using the Products of this Invention

In current blood banking practice, where platelet concentrate (PC) is desired to be recovered, the sequence of operation is:

a. Perform venipuncture and draw about 400 to about 450 ml of blood into a sterile collector bag in which an anti-coagulant has been preplaced. This collection bag is attached by tubing to two other bags via a tee connection, these bags denoted respectively as the platelet bag and the plasma bag.

b. The collector bag is then placed in a centrifuge and spun for about 3 minutes at conditions which develops about 2000 G (i.e., 2000 times the force due to gravity) during which the red cells are concentrated, forming the PRC at the bottom of the bag.

c. The collector bag is then placed in a device which is denoted as an "expresser", but in one commonly used version is denoted as a "plasma extractor". The expresser squeezes the bag, developing about 1 to about 1.5 psi of internal pressure. The operator opens a valve at the top of the bag, allowing the supernatant fluid containing the plasma and most of the platelets to be decanted into the platelet bag, and leaving in the collection bag about 170 to about 250 ml of PRC. It is this PRC which is, in a separate step, processed by the filter of this invention in order to reduce its leucocyte content.

d. The remaining steps in the blood processing as generally practiced are preparation of plasma, or of platelet concentrate and plasma. These are not described, as they are not pertinent to this invention.

In alternate types of procedure, for example those designated as Adsol or SAG-M, the procedure of steps 1, 2 and 3 is similar except that a harder (higher G) spin may be used, and after decanting the supernatant liquid in an expresser, the red cells are resuspended in a physiological solution containing saline and an anti-coagulant, forming the PRC.

In the practice of this invention, the collected PRC prepared by these or similar processes is as the next step passed through the filter of this invention. This may be done in a separate step in which a filter and second collecting bag are aseptically attached to the PRC bag, and the PRC is forced, for example by a pressure cuff developing a pressure of about 0.4 Kg/cm², to pass through the filter into the second collection bag. Alternatively the filter and the second collection bag may be attached to the lower end of the whole blood collection bag prior to collecting the blood from the donor; then, after the supernatant fluid in the blood collection bag has been removed by centrifuging and decanting, and while the bag is still in the expresser, the PRC is transferred through the filter into the second collection bag using the pressure provided by the expresser.

EXAMPLES

All tests run used blood drawn from human volunteers and processed using either Adsol CPDA-1 anticoagulant within 6 hours in accordance with the standards of the American Association of Blood Banks to provide one unit of PRC. Hematocrits of the PRC were recorded and were with few exceptions in the range of about 70 to about 80%, while hematocrits of Adsol processed blood were generally in the range of about 55 to 65%. Leucocyte counts of the PRC prior to processing were in the range of about 1500 to about 17,000 per microliter (μL).

Priming time is defined as the time required to fill the test housing with fluid.

Bag (i.e., influent) leucocyte counts were determined using a Model ZM Coulter Counter. Leucocyte counts are reported as number per microliter (μL). The conventional centrifugal method was used to determine hematocrits.

Use of automatic counters for the leucocyte depleted filter effluents provides incorrect results because automatic counters are designed to be operated in the range of normal leucocyte content of whole blood and of normal PRC. Thus, the normal operating range of automatic counters is about $10^3$ to about $10^7$ times the levels reached in the examples herein; as a consequence, automatic counter data at these low levels is quite useless.

A method to assay the degree of depletion of leucocytes to the very low levels of this invention, i.e., reduction of leucocyte count by a factor between about $10^5$ to about $10^7$ (99.999 to 99.99999% efficiency) has become available only recently. The method was developed, in a cooperative project with Pall Corporation (Pall), by the laboratory of the American Red Cross (ARC). Pall supplied the necessary high efficiency filters, while the ARC developed the assay method. This assay method, subsequently routinely practiced in the Pall blood laboratory, is described below.

Zeta potential was determined using a conventional streaming potential apparatus.

The elements used in the examples were right circular discs, about 88.9 mm in diameter at assembly. The stacked layers of elements, with a total thickness of t cm were assembled into a housing as described above, with a clearance of about t cm between the faces of the two plenums, i.e., between the tips of the ridges 26 on the inlet plate 20 and the tips of the ridges 34 on the outlet plate 31, as shown in FIG. 1. After piercing the blood bag, leucocyte content was determined in the manner described in the preceding part of this section.

Losses of red cells due to adsorption were, unless noted, too small to be detected. For the examples of this invention losses due to hold-up within the filter housing were about 30 $cm^3$ of PRC.

Pore diameters of filter media were determined using the modified OSU F2 method and are reported as the diameter of hard particle at which about 99.9% of the incident particles were removed. The F2 test used in making pore size measurements is a modified version of the F2 test developed in the 1970's at Oklahoma State University (OSU). In the OSU test, a suspension of an artificial contaminant in an appropriate test fluid is passed through the test filter while continuously sampling the fluid upstream and downstream of the filter under test. The samples are analyzed by automatic particle counters for their contents of five or more preselected particle diameters and the ratio of the upstream to downstream count is automatically recorded. This ratio is known in the filter industry as the beta ratio.

The beta ratio for each of the five or more diameters tested is plotted as the ordinate against particle diameter as the abscissa, usually on a graph in which the ordinate is a logarithmic scale and the abscissa is a log 2 scale. A smooth curve is then drawn between the points. The beta ratio for any diameter within the range tested can then be read from this curve. Efficiency at a particular particle diameter is calculated from the beta ratio by the formula:

Efficiency, percent=100(1—1/beta)

As an example, if beta=1000, efficiency=99.9%.

The removal rating cited in the examples presented herein is the particle diameters at which beta=1,000, hence, the efficiency at the removal ratings cited is 99.9%.

In the modified F2 test, efficiencies in particles in the range of from about 1 to about 20–25 μm were determined using as a test contaminant an aqueous suspension of AC fine test dust, a natural silicious dust supplied by the AC Spark Plug Company. A suspension of the dust in water was vigorously mixed for three weeks until the dispersion was stable. Then, prior to use for measuring the pore size characteristics, the suspension was passed through one of the gel prefilters of this invention, thereby removing oversize particles which would otherwise collect on the filter surface and cause flow to stop. Pore diameter values below 1 μm were obtained by extrapolation per the following tabulation:

| Beta Value at 1 μm | Pore Diameter (μm) |
|---|---|
| 1000–2000 | 1 |
| 1200–1800 | 0.9 |
| 1800–2500 | 0.8 |
| 2500–4000 | 0.7 |

Test flow rate was 100 liters per minute per square foot of filter area and each pore size measurement as reported is the average of four tests.

The needle punched web used in the examples was scrubbed in order to remove the fiber lubricant, and then dried.

Preform thickness was measured using a 7.7 cm diameter anvil and with an applied pressure of 4.3 $g/cm^2$.

Unless otherwise noted all of the elements used in the examples were right circular discs of diameter 88.9 mm at assembly. Properties of sub-sections of composite discs are listed in the order in which the blood flow through them.

Gel prefilter type A consisted of three layers. The two upper layers consisted of 8±1 $mg/cm^2$ of 23 μm average fiber diameter PET needle punched web, while the third and last layer consisted of a 7.7 $mg/cm^2$ 20 μm average fiber diameter PBT melt blown web. The first of the three layers was hot calendered to about 0.89 cm thick by passing the web between a pair of moving belts in an oven in order to heat the web to about 165° to about 170° C., following which it passed through calendering rolls. The second and third layers were hot calendered in assembly to about 0.10 cm thick. All of the above were then hot calendered together to a thickness of about 0.13 cm. The resulting gel prefilter consisted of 3 integrated layers of approximate density, respectively, 0.14, 0.19, and 0.32 $g/cm^2$, the last layer having a pore diameter of about 20 to about 30 μm.

Gel prefilter type B consisted of four adjacent layers of about 20 μm diameter fiber melt blown web each separately hot calendered in the manner described above to obtain the characteristics listed below:

| Weight mg/cm² | Thickness cm | Voids Volume, % |
|---|---|---|
| 3.1 | .025 | 91 |
| 4.1 | .025 | 88 |
| 5.7 | .025 | 84 |
| 7.7 | .025 | 78 |

Although the thickness of the separately measured layers of the type B prefilter add up to about 0.1 cm, the total thickness when the four were stacked on each other was about 0.08 cm. The last layer had a pore diameter of about 20 to about 30 μm.

All type B gel prefilters were made using PBT fibers with no surface modification.

The development procedure went through stages at which first a laboratory (L) method was used to achieve hot compression, and later a production (P) method was used to achieve the same purpose. In the L method the necessary microaggregate filter and adsorption filter layers were assembled as a stack and the whole compressed between Teflon lined aluminum alloy plates at 165° C. for about 40 seconds. In the P method a similar stack was passed between two moving Teflon coated belts heated to about 165° to about 170° C. for a period of about 30 seconds, following which they were passed through a pair of calender rolls to achieve the desired density or thickness.

The filter effluents were assayed to determine leucocyte content using a "Ficoll" method, alternatively referenced hereinafter as the "ARC" method, in which the leucocytes are separated in concentrate form enabling a high proportion of all of the leucocytes present to be counted directly. This method was developed in the laboratory of the American Red Cross. Prior to this development no assay procedure was available which was capable of counting the very low levels of leucocytes, less than about $10^2$ to about $10^5$ per unit of PRC, which are obtained using the products of this invention. The Ficoll Assay is described below:

1.0 Purpose 1.1 This test method is used to separate leucocytes from filtered packed red cells and determine the log efficiency of a leucocyte depleting filter.

2.0 Materials and Equipment one unit of fresh PRC or of whole blood 5 mL disposable polypropylene test tubes with caps 600 mL transfer bags filter pressure infusor hemastat clamps 500 mL graduated cylinder Ficoll solution (see section 4.4)

60 mL disposable polypropylene syringe plasma extractor

Sorvall RC-3C General Purpose Refrigerated Centrifuge blood bank pipets vacuum suction apparatus 1% ammonium oxalate solution (see section 4.3)

aliquot mixer

Neubauer hemacytometer plain hematocrit tubes

Fluorescent microscope with phase contrast and 20 and 40X objectives 250 mL disposable polypropylene centrifuge tubes 15 mL disposable polypropylene centrifuge tubes hematology control: normal level and low abnormal level—Counter-Check™, Diagnostic Technology, Inc.

Acridine orange fluorescent stain (see Section 4.4)

3.0 Procedure 3.1 Mix the PRC unit and withdraw a sample in a 5 mL tube for use to count influent leucocytes.

3.2 Connect the pre-weighed 600 mL transfer bag to the filter outlet, and the filter inlet to the blood bag.

3.3 Prime the filter with PRC using a pressure infusor set at 300 mm Hg.

3.4 When flow has begun, lower pressure to 200 mm Hg for remainder of filtration.

3.5 When filtration is complete, turn pressure off, clamp the collection bag and remove it from the filter.

3.6 Determine the effluent volume by weighing the collection bag, subtracting the empty bag weight, and dividing by 1.08 (the density of PRC). Record this volume.

3.7 Adjust the volume to 300 cc by discarding the excess, or by adding saline, then remove the syringe and seal off the bag.

3.8 With a graduated cylinder, measure 300 cc of Ficoll solution and add it to the collection bag using a 60 mL syringe attached to the transfer bag tubing.

3.9 Vigorously mix the Ficoll-blood solution and place the bag in a plasma extractor.

3.10 Clamp the tubing and remove the syringe.

3.11 Apply the extractor clamp and let the blood settle for 30 minutes.

3.12 Carefully express the upper layer into a 250 mL centrifuge tube by opening the hemastat clamp. Do not disturb the interface while expressing the maximum amount of Ficoll.

3.13 Release the extractor clamp and repeat step 3.8 using a sufficient volume of Ficoll to fill the 600 ml bag, then repeat 3.9, 3.10, 3.11, and 3.12.

3.14 Centrifuge the tubes at 775 g for 15 minutes at room temperature in the Sorvall™ centrifuge.

3.15 When spin is complete, use a blood bank pipet attached to a vacuum flask to extract and discard the supernatant leaving a red pellet.

3.16 Resuspend the pellet in 250 mL of 1% ammonium oxalate.

3.17 Allow the suspension to mix on an aliquot mixer for 10 minutes to lyse the red blood cells.

3.18 Centrifuge the tube at 432 g for 10 minutes at room temperature and discard the supernatant as before.

3.19 Resuspend the pellet in 2–3 mL of ammonium oxalate using a blood bank pipet to draw the pellet up for mixing. Transfer this suspension to a 15 mL polypropylene centrifuge tube combining all pellets from one blood unit.

3.20 Fill the tube to the 15 mL mark with the 1% ammonium oxalate solution, mix, and allow tube to set for 10 minutes.

3.21 Spin the 15 mL tube in the centrifuge at 775 g for 10 minutes at room temperature.

3.22 Decant the supernatant down to the 0.5 mL line on the 15 mL tube. Carefully resuspend the pellet using a pipetter. Add 0.05 mL of Acridine Orange stain to the suspension, and weigh and record the tube weight to determine the final volume of the suspension.

3.23 Leucocyte Counts: All counts are performed manually 3.23.1 Control Counts 3.23.1.1 Control counts are performed daily by making a 1:100 dilution of each control in 1% ammonium oxalate.

3.23.1.1.1 Add 0.01 mL of the control to 0.99 mL of 1% ammonium oxalate using an adjustable pipetter. Mix well and let the dilution sit for at least 10 minutes to lyse the red blood cells, then add 0.05 mL of Acridine Orange.

3.23.1.1.2 Charge each side of a hemacytometer using a plain capillary tube, taking care not to overload or underload the chamber.

3.23.1.1.3 Allow the hemacytometer to sit in a moist atmosphere (covered petri dish with moistened filter paper in bottom half of the dish) for ten minutes.

3.23.1.1.4 Count the number of leucocytes in the nine large squares on both sides of the hemacytometer using the phase contrast UV microscope.

3.23.1.1.5 Record the counts from each side (each nine squares) of the hemacytometer.

3.23.1.1.6 To determine the number of leucocytes/µL, use the following formula:

$$\text{leucocytes/µL} = \frac{\text{total cells counted}}{\text{total squares counted}} \times \text{dilution} \times 10$$

(if 18 large squares are counted, the total number of cells counted × 56 = cells/µL)

3.23.2 Influent Leucocyte Counts 3.23.2.1 Influent leucocyte counts are performed using the same procedure as for the control counts except that a total of 36 large squares (two hemacytometers) are counted.

3.23.2.2 To calculate the leucocytes/µL, use the same formula as above. If 36 large squares are counted, the total number of cells×28=cells/µL.

3.23.2.3 The number of leucocytes/μL×1000 equals the number of leucocytes/mL.

3.23.2.4 Multiply the number of leucocytes/mL by the effluent volume to determine the total leucocytes in the prefiltration sample (note: the effluent volume is used in this calculation, not the influent volume, because log reduction is a direct volume/volume comparison and does not take into account the hold-up volume).

3.23.3. Effluent Leucocyte/Counts 3.23.3.1 Effluent leucocyte counts are performed using he undiluted final ammonium oxalate suspension from step 3.24.

3.23.3.1.1 Charge the hemacytometer and count as before.

3.23.3.1.2 If the number of cells counted on both sides of the hemacytometer is 30 or less, continue counting hemacytometers until 30 cells or 5 hemacytometers are counted.

3.23.3.2 Determine the total leucocytes in the post-filtration sample as follows:

3.23.3.2.1 Divide the effluent volume by the volume of the final suspension to determine the concentration.

3.23.3.2.2 Use the following formula to calculate leucocytes/μL:

$$\frac{\text{total cells counted}}{\text{total squares counted}} \times \frac{1}{\text{concentration} \times 10}$$

3.23.3.2.3 The number of leucocytes/μL×1000 equals the number of leucocytes/mL.

3.23.3.2.4 Multiply the number of leucocytes/mL by the effluent volume to get the number of leucocytes in the postfiltration sample.

3.23.3.2.5 The Ficoll procedure gives a nominal 53% yield of leucocytes, thus the number from the step above must be divided by 0.53 to determine the total leucocytes in the postfiltration sample.

3.24 Determine the log reduction by dividing the total number of leucocytes in the prefiltration sample by the total number of leucocytes in the postfiltration sample and taking the log of this quotient.

4.0 Supplementary Information 4.1 Ficoll Formula

| | |
|---|---|
| 100.0 g | Ficoll* 400 DL |
| 20.0 g | Bovine Serum Albumin |
| 2000.0 mL | Stock EBSS (see below) |

Mix the above ingredients in a 2 L volumetric flask and warm to 37° C. while stirring. Filter solution through a 1.2 μm filter disc and then through a 0.45 μm filter disc. Store at 4° C.

*Ficoll 400 DL is a dialyzed, hydrophilized, synthetic polymer of sucrose with a molecular weight of approximate 400,000 available from Sigma Chemical Co.

4.2 Stock EBSS Formula 200.0 mL Earle's Balanced Salt Solution (10×)

1800.0 mL deionized $H_2O$ 40.0 mL Hepes Buffer Solution

Mix the above ingredients and store at 4° C. Warm to room temperature prior to use.

4.3 Ammonium Oxalate Formula 10.0 g Ammonium Oxalate 0.10 g Thimerosal 0.43 g KH2PO4

0.57 g Na2HPO4

Mix the above ingredients in a 1 L volumetric flask and dilute to 1 L with deionized water. Check the pH and adjust to 6.8 if necessary. Store at 4° C. Warm to room temperature prior to use.

4.4 Acridine Orange Stain Formula 4.4.1 Stock Acridine Orange (1000×solution)

6.69 mg Acridine Orange/ml of DI water

Store in the dark at 2°–5° C.

4.4.2 Working Acridine Orange (10×solution)

dilute Stock Acridine Orange with Stock EBSS (see 4.2)

good for 1 month if stored in the dark at 2°–5° C.

The above described assay method has a nominal recovery efficiency of 53% of the leucocytes actually present in the filtered PRC. The consistency of the 53% figure is about +15 to −25%; however, the log reduction calculated is affected in only a minor way by these deviations when a single test is run, and consistency is improved by running four or more tests on each filter tested.

The leucocyte removal efficiencies obtained for the products of this invention using the ARC assay procedure can be stated in several alternate ways. Using as an example a unit of PRC containing $10^3$ leucocytes in the total filtrate, and a value of $10^9$ leucocytes contained in an equal volume of the PRC prior to filtration, then the ratio of effluent content/influent content is $10^3/10^9 = 10^{-6}$, and efficiency of leucocyte removal can be reported as:

(a) $100(1-10^{-6})=99.9999\%$ or (b) leucocyte content is reduced by a factor of one million $(1/10^{-6}=10^6)$ or (c) log reduction=−6

A convenient method is to use the term log reduction and omit the minus sign, since minus is inferred by the term "reduction". This nomenclature is widely used, and we will use it when reporting efficiencies hereinafter.

Examples 1–6 were performed in the ARC laboratory using preformed filter elements prepared in the inventors' laboratory by Pall Corporation personnel using materials and procedures conceived and developed by the inventors with no input from ARC. ARC's contribution to this part of the development was confined to developing and initially performing the Ficoll test on filters developed and made by Pall, and then reporting test results to the Applicant. Later the Ficoll test was performed in Pall's laboratory using Pall personnel.

This group of examples consisted of a single preform made using 2.6 μm fiber diameter melt blown PBT web, hot compressed using the L (laboratory) technique described above. No prefiltration was used. The tests were run using 47.6 mm diameter discs, assembled into Pall made housings of slightly smaller diameter. Each test was run using one quarter of a unit of fresh PRC of hematocrit 50 to 55%. Flow rate of 4 to 8 cc per minute was obtained at a pressure of 40 inches of fluid head. The resulting data for these examples is listed in Table 1. When plotted, 5 of the 6 points fall on or near to a straight line represented by the equation $$\text{Log reduction} = 18.5\rho + 0.5 \text{ OR} \tag{1}$$

$$\rho = \frac{\text{Log reduction} - 0.5}{18.5}$$

where ρ is the density in grams/cc, and the weight of the adsorption/filtration element is $$(0.5\rho - 0.029)\text{g/cm}^2 \tag{2}$$

This equation provides guidance for selecting the densities of PBT filters which have a desired average log reduction between about 4.5 to about 7; however, filters with log reduction in the upper part of the range, with voids volumes less than about 74% to about 78%, may become clogged prior to passage of a single unit of PRC, consequently gel, microaggregate filters, or multilayers may be required to prevent occational clogging.

In example 7, ten discs with a pore diameter of 0.9 μm duplicating those of Example 4, except 88.9 mm in diameter, are assembled into an 88.6 mm diameter housing with ridge to ridge depth of 0.439 cm. Priming is accomplished in 50 to 100 seconds at a pressure of 0.4 Kg/cm², and one full unit of fresh PRC of hematocrit of 70 to 80% derived from blood collected into CPDA-1 anticoagulant is passed through each at a pressure of 0.27 Kg/cm². The average time to pass one unit through five of the ten discs ranges from 15 to 25 minutes. The average log reduction is approximately 6.4. Flow in the other five of the ten tests will fall within a 2 hour period to less than 0.7 cc/min, and these tests are then discontinued.

In Example 8, ten integral preformed discs duplicating those of Example 7 are assembled together with a type A gel prefilter into an 88.6 mm diameter housing with ridge to ridge depth of 0.569 cm, and one unit of fresh PRC will be passed through each. The total volume of one unit of PRC is passed at a pressure of 0.27 Kg/cm² in 15 to 25 minutes. The average log reduction is approximately 6.4.

In Example 9, ten discs duplicating those of Example 7 are assembled together with a type B gel prefilter into an 88.6 mm diameter housing with ridge to ridge depth of 0.519 cm, and one unit of fresh PRC is passed through each in the same manner as in Example 7. The total volume of PRC is passed in 15 to 25 minutes. The average log reduction is approximately 6.4.

In Examples 8 and 9 the addition of the type A and B prefilters will make clogging less likely than would be the case if they were not used, as in Example 7.

Example 10 is prepared in the same way as Example 9, except that the adsorption/filtration element is integral with a microaggregate filter, formed by including two layers of media of larger fiber diameter in the upstream side of the lay-up, followed by hot compression to obtain a preformed integral element. Specifically, the uppermost layer is made using 3.2 μm diameter fibers in the form of a mat of weight 0.0065 g/cm², and the adjacent layer is made using 2.9 μm diameter fiber of weight 0.0069 g/cm², while the balance, the adsorption/filtration element consists of multiple layers, all of fiber diameter 2.6 μm. Total weight is 0.130 g/cm² compressed to a voids volume of 76.5% (density=0.324 g/cc) and thickness of 0.439 cm. The filter so made will possess capability for microaggregate removal, and be more resistant to clogging, as would otherwise be caused by the occasional specimen of donated blood which contains an unusually high content of microaggregates. The properties of the filter of Example 10 with respect to efficiency of leucocyte depletion and blood transit time are not significantly altered from those of Example 9, as the fiber surface area of Example 10 is reduced from that of Example 9 by only about 1%. The pore sizes obtained by F2 testing are essentially equal for the two examples. Blood hold-up volume within the voids of the gel prefilter, the microaggregate prefilter, and the adsorption/filtration element are, respectively, 3.9 cc, 1.6 cc, and 19.1 cc for a total of 24.6 cc.

Examples 11 to 14, summarized in Table 2, illustrate the use of equations (3) and (4) set forth above to calculate the manner in which filter assemblies may be made which have lower efficiencies, but which during filtration pass PRC at a lower pressure drop, making it possible to use gravity to induce flow at a satisfactory rate when processing blood with relatively high hematocrit. All contain integral elements combining microaggregate elements with adsorption/filtration elements, with the fibers surface modified to a CWST of 60 to 70 dynes/cm, and preferably 62 to 68 dynes/cm. The device of Example 11 also incorporates a type B gel prefilter.

Other variations of density and thickness are possible. All of the Examples 11–14 can be made with a higher density (i.e. lower voids volume), while retaining equal or better leucocyte removal efficiency. Thus, Example 15 is made in the same manner as Example 11 except that the voids volume is changed to 76.5%. The resulting log leucocyte reduction will be intermediate between 6 and 6.5, and the blood hold-up volume within the element is reduced by about 10%. Similarly, Example 16 is the filter of Example 12 with the voids volume decreased from 80.4 to 78.5%, with log reduction between 5.5 and 6, and blood hold-up volume reduced by about 10%, and Example 17 is the filter of Example 13 with voids volume decreased from 82.4 to 80.4%, with log reduction between 5 and 5.5, and with blood hold-up volume decreased by about 10%. Example 18 is the filter of Example 14 with voids volume decreased from 84.3 to 82.4%, with log reduction between 4.5 and 5, and with blood hold-up volume decreased by about 11%.

The void volume of each of Examples 16, 17, and 18 could be further decreased, obtaining in this way equal or higher efficiency along with still lower blood hold-up volume compared with Examples 16, 17, and 18.

Example 19 is essentially the filter of Example 10 with voids volume decreased further. A type B prefilter was used in this construction in order to minimize the chances of clogging. Immediately downstream of the prefilter was a section consisting of nine layers, all of fiber diameter 2.6 μm, with a CWST of 66 dynes/cm and a total weight of 0.054 g/cm², compressed to a voids volume of 77% (density=0.321 g/cc) and a thickness of 0.168 cm. Another section, downstream of this one, consisted of 20 layers of the same type of fibers, however, compressed to a lower voids volume. The total weight of this section was 0.118 g/cm², voids volume was 70% (density=0.414 g/cc), and thickness was 0.285 cm. When tested with blood in accordance with the previous examples, this combination gave a leukocyte reduction of 6 log, and a total filtration time of 32 minutes.

It was previously thought that the use of voids volumes much below about 74% would pass PRC more slowly and thus would tend to clog with higher frequency. However, another surprising feature of this invention is that voids volumes of 70% were found to be quite suitable and efficient, and voids volumes as low as 60% may be useful for some special applications. When lower voids volumes are utilized, it is found that it is the combination of voids volumes with other factors, i.e., the number of multilayers in each section, rather than a particular voids volume by itself, that produces an element that is suitable in carrying out the instant invention.

While the examples all deal with PRC, generally equivalent results will be obtained when anticoagulated whole blood is used.

An extraordinary and very surprising feature of this invention is the ability of red blood cells to pass through a filter of pore diameter less than 1 μm without apparent injury and no apparent losses. The ability to use such small pored filters was not anticipated, and was seen only as a very unlikely possibility meriting exploration in the absence of other approaches to the preferred goal of 100,000 to 1,000,000 fold reduction of leucocyte content in a filter so small that red cell loss due to hold-up is less than 10% of the average volume of a unit of PRC.

Red cell loss can be reduced by passing saline post filtration into or through the filter. Passing a volume about equal to that of the filter helps to reclaim blood. It is generally a less desirable procedure to flush the filter with larger volumes of saline, as this undesirably increases blood volume and may reduce efficiency by flushing out some white cells. Use of saline requires manipulation which is relatively costly in terms of labor, while at the same time compromising sterility of the red cell concentrate. For these reasons, small hold-up volume, with correspondingly small red cell loss, is very desirable, as it obviates the need for using saline.

The adsorption/filtration elements described in the examples of this invention all comprise a non-woven web of average fiber diameter 2.6 µm. Of the various media available to the inventors, this was selected because it can be made in large quantity with very reproducible properties. Should smaller fiber diameter webs become available in the future, or if such exist elsewhere at this time, these may be adapted by one versed in the art of filter development to be used in the manner described above possibly with advantage. A product so developed would fall within the scope of this invention.

Products resembling and similar in function to those of this invention may be made using coarser fibers. Such a product may perform similarly in a general way to the product of this invention, and would fall within the scope of this invention.

Similarly, other materials and methods of surface modification may be used to achieve similar results, but these also would be within the scope of this invention.

We claim:

1. A device for the depletion of the leukocyte content of a blood product comprising a fibrous leukocyte adsorption/filtration filter having a pore diameter of from about 0.5 to about 2 µm, a negative zeta potential, and a CWST of from about 60 to about 70 dynes/cm.

2. A device according to claim 1 which further comprises a microaggregate filter upstream from the fibrous leukocyte adsorption/filtration filter.

3. A device according to claim 1 in which the fibrous leukocyte adsorption/filtration filter is disposed in a housing having an inlet and an outlet and defining a blood product flow path between the inlet and the outlet, wherein said filter is disposed within the housing across the blood product flow path, and wherein the device has a total voids volume of less than about 30 cc.

4. A device according to claim 1 in which the fibers of the fibrous leukocyte adsorption/filtration filter have been radiation grafted with a monomer containing a hydrophilic group.

5. The device of claim 1 wherein the fibrous leukocyte absorption/filtration filter is preformed to controlled density and pore diameter.

6. The device of claim 1 wherein the filter has a CWST of from about 62 to about 68 dynes/cm.

7. The device of claim 1 wherein the filter further comprises at least one of a gel prefilter and a microaggregate filter.

8. The device of claim 1 wherein the filter has a voids volume in the range of about 65% to about 84%.

TABLE 1

Adsorption/Filtration Element Only (No Prefiltration) - 2.6 µm dia. fiber

| Example No. | No. of Tests | CWST dynes/cm | Blood hold-up volume, cc** | Zeta Potential millivolts | Weight, g/cm² | Thickness, cm | Density g/cc | Voids Volume, % | Pore dia., micrometers | Average Leukocyte log Reduction |
|---|---|---|---|---|---|---|---|---|---|---|
| 1 | 4 | 63 | 20.0 | −30 to −40 | .103 | .399 | .259 | 81.2 | 1.2 | 5.4 |
| 2 | 8 | 63 | 19.2 | −30 to −40 | .092 | .379 | .244 | 82.3 | 1.4 | 4.4 |
| 3 | 8 | 63 | 19.7 | −30 to −40 | .089 | .384 | .233 | 83.1 | 1.5 | 4.8 |
| 4 | 8* | 70 | 20.7 | −2 to −12 | .143 | .439 | .324 | 76.5 | 0.9 | 6.4 |
| 5 | 4 | 70 | 21.5 | −2 to −12 | .123 | .439 | .281 | 79.6 | 1.2 | 6.0 |
| 6 | 7 | 70 | 19.1 | −2 to −12 | .104 | .386 | .269 | 80.5 | 1.2 | 5.5 |

*Clogging prior to complete passage of the PRC was observed in 4 of eight tests.
**Internal voids volume of the disc, calculated for a full size 88.6 mm diameter disc.

TABLE 2

Filters with log reduction 4.5 to 6, and with reduced internal blood hold-up

| 1 Example No. | 2 Weight, g/cm² | 3 Thickness, cm | 4 Density, g/cc | 5 Voids Volume, % | 6 Pore dia., µm | 7 Blood hold-up volume within filter elements, cc | 8 Log Reduction |
|---|---|---|---|---|---|---|---|
| 11 | .119 | .400 | .297 | 78.5 | 1.0 | 24.4* | 6 |
| 12 | .106 | .392 | .270 | 80.4 | 1.2 | 19.7 | 5.5 |
| 13 | .092 | .379 | .243 | 82.4 | 1.4 | 19.4 | 5.0 |
| 14 | .079 | .366 | .216 | 84.3 | 2.0 | 19.1 | 4.5 |

*Includes gel prefilter type B

9. The device of claim 1 wherein the filter has a pore diameter of about 2 μm.

10. The device of claim 1 further comprising a fibrous gel prefilter and a fibrous microaggregate filter.

11. The device of claim 10 wherein the fibrous microaggregate filter is interposed between the fibrous gel prefilter and the fibrous leukocyte adsorption/filtration filter.

12. The device of claim 1 wherein the fibrous leukocyte adsorption/filtration filter includes fibers having an average diameter of about 3 μm or less.

13. The device of claim 1 wherein the fibrous leukocyte adsorption/filtration filter has fibers that have been radiation grafted with at least one acrylic monomer;

14. The device of claim 13 wherein the fibrous leukocyte adsorption/filtration filter has fibers that have been radiation grafted with first and second acrylic monomers.

15. The device of claim 14 wherein the first acrylic monomer is methyl acrylate or methyl methacrylate.

16. A device for the depletion of the leukocyte content of a blood product comprising:

a fibrous microaggregate filter; and a leukocyte adsorption/filtration filter having a pore diameter of from about 0.5 to about 2 μm, a negative zeta potential, and a CWST of from about 55 to about 80 dynes/cm.

17. The device of claim 16 wherein the leukocyte absorption/filtration filter is compressed to an average voids volume of about 60% to about 85%.

18. The device of claim 17 wherein the leukocyte absorption/filtration filter is compressed to an average voids volume of about 65% to about 74%.

19. A device according to claim 16 in which the leukocyte adsorption/filtration filter is hot compressed to an average voids volume of about 65% to 84%.

20. A device according to claim 16 in which the fibrous microaggregate filter comprises a fibrous web compressed to an average voids volume of about 74% to about 84%.

21. The device of claim 16 wherein the leukocyte adsorption/filtration filter has a pore diameter of about 2 μm.

22. The device of claim 16 wherein the fibrous microaggregate filter and the leukocyte adsorption/filtration filter each include multilayers.

23. The device of claim 22 wherein the leukocyte adsorption/filtration filter includes nine or more layers.

24. The device of claim 22 wherein the leukocyte adsorption/filtration filter includes two sets of multilayers.

25. The device of claim 22 wherein the fibrous microaggregate filter has a CWST of from about 55 to about 80 dynes/cm.

26. The device of claim 25 wherein the leukocyte adsorption/filtration filter has a CWST of from about 60 to about 70 dynes/cm.

27. The device of claim 26 wherein the leukocyte adsorption/filtration filter has a CWST of from about 62 to about 68 dynes/cm.

28. The device of claim 16 wherein the leukocyte adsorption/filtration filter is capable of depleting the leukocyte content of whole blood.

29. The device of claim 16 wherein the leukocyte adsorption/filtration filter is capable of depleting the leukocyte content of fresh whole blood.

30. The device of claim 16 further comprising a housing including an inlet and an outlet and defining a blood product flow path between the inlet and the outlet, said fibrous microaggregate filter and said leukocyte absorption/filtration filter disposed within the housing across the blood product flow path, wherein the fibrous microaggregate filter and the leukocyte absorption/filtration filter are arranged to deplete the leukocyte content of the blood product by a factor of at least about 30,000.

31. The device of claim 16 wherein the leukocyte adsorption/filtration filter has fibers that have been radiation grafted with a monomer containing a hydrophilic group.

* * * * *